US012599707B2

(12) United States Patent
Brassil

(10) Patent No.: US 12,599,707 B2
(45) **Date of Patent: *Apr. 14, 2026**

(54) COATING FOR MEDICAL DEVICES

(71) Applicant: SMART REACTORS SERVICE LIMITED, Galway (IE)

(72) Inventor: Mark Brassil, Galway (IE)

(73) Assignee: SMART REACTORS SERVICE LIMITED, Galway (IE)

( * ) Notice: Subject to any disclaimer, the term of this patent is extended or adjusted under 35 U.S.C. 154(b) by 956 days.

This patent is subject to a terminal disclaimer.

(21) Appl. No.: 17/779,788

(22) PCT Filed: Nov. 6, 2020

(86) PCT No.: PCT/EP2020/081383
§ 371 (c)(1),
(2) Date: May 25, 2022

(87) PCT Pub. No.: WO2021/104835
PCT Pub. Date: Jun. 3, 2021

(65) Prior Publication Data

US 2023/0018889 A1 Jan. 19, 2023

(30) Foreign Application Priority Data

Nov. 30, 2019 (GB) ...................................... 1917529

(51) Int. Cl.
*A61L 31/10* (2006.01)
*A61L 29/08* (2006.01)
(Continued)

(52) U.S. Cl.
CPC ............... *A61L 31/10* (2013.01); *A61L 31/16* (2013.01); *A61L 33/064* (2013.01); *A61L 29/08* (2013.01);
(Continued)

(58) Field of Classification Search
CPC ...... A61L 29/08; C08F 222/02; C08F 220/04; C08F 8/36; C08L 33/08; C08L 33/10
See application file for complete search history.

(56) References Cited

U.S. PATENT DOCUMENTS 5,278,200 A 1/1994 Coury et al.
6,160,056 A 12/2000 Jozefowicz et al.
(Continued)

FOREIGN PATENT DOCUMENTS

CN 110343284 A 10/2019
DE 4022695 A1 1/1992
(Continued)

OTHER PUBLICATIONS

Office Action of Japanese Patent Application No. 2022-532032 (Publication No. 2023-504137) dated Nov. 12, 2024, and its English translation.
(Continued)

*Primary Examiner* — Kregg T Brooks
*Assistant Examiner* — David R. Foss
(74) *Attorney, Agent, or Firm* — Squire Patton Boggs (US) LLP

(57) ABSTRACT

A coating for a medical device is described. The coating comprises: a surface layer; and optionally a base layer; wherein the surface layer comprises a polymer chain attached to an anti-clotting group, wherein the anti-clotting group is selected from a sulfonic acid group, a sulfonamide group, a sulfamic acid group, a hydrogen sulfate group and a conjugate base thereof. Also described is a medical device comprising the coating, and uses and methods involving the coating and the medical device.

15 Claims, 10 Drawing Sheets

(51) Int. Cl.

| | |
|---|---|
| ***A61L 31/16*** | (2006.01) |
| ***A61L 33/06*** | (2006.01) |
| ***C08F 8/36*** | (2006.01) |
| ***C08F 220/04*** | (2006.01) |
| ***C08F 222/02*** | (2006.01) |
| ***C08L 33/08*** | (2006.01) |
| ***C08L 33/10*** | (2006.01) |

(52) U.S. Cl.

CPC ............ *A61L 2300/42* (2013.01); *C08F 8/36* (2013.01); *C08F 220/04* (2013.01); *C08F 222/02* (2013.01); *C08L 33/08* (2013.01); *C08L 33/10* (2013.01)

(56) References Cited

U.S. PATENT DOCUMENTS

| | | | | |
|---|---|---|---|---|
| 2005/0025799 | A1* | 2/2005 | Hossainy ................ | A61L 31/10 424/423 |
| 2008/0075753 | A1* | 3/2008 | Chappa .................. | A61L 27/34 424/426 |
| 2014/0172117 | A1 | 6/2014 | Anzai et al. | |

FOREIGN PATENT DOCUMENTS

| | | | |
|---|---|---|---|
| EP | 0 093 489 | A2 | 11/1983 |
| EP | 2749302 | A1 | 7/2014 |
| JP | H04208165 | A | 7/1992 |
| JP | H06206935 | A | 7/1994 |
| KR | 10-2004-0065348 | | 7/2004 |
| WO | WO 2013/027556 | A1 | 2/2013 |

OTHER PUBLICATIONS

Brynda et al. "Albumin and heparin multilayer coatings for blood-contacting medical devices", Journal of Biomedical Materials Research, Aug. 2000, vol. 51, No. 2, pp. 249-257.

Brynda et al., "Albumin and heparin multilayer coatings for blood-contacting medical devices", Journal of Biomedical Materials Research, Wiley, New York, NY, US, vol. 51, No. 2, Aug. 1, 2000 (Aug. 1, 2000), pp. 249-257, XP002370547, ISSN: 0021-9304, DOI: 10.1002/(SICI)1097-4636(200008)51:2 249::AID-JBM143.0.CO;2-X.

Examination Report for EP Application 20803556.8-1109, issued Feb. 23, 2024.

Chinese Application No. 202080093989.9 Office Action issued Dec. 28, 2023.

Interantional Search Report and Written Opinion of PCT/EP2020/081383 mailing date of Feb. 9, 2021; 9 pages.

Patent Act 1977: Combined Search and Examination Report under Section 17 and 18(3) of Application No. GB2017715.0 dated Dec. 22, 2020; 7 pages.

* cited by examiner

COATING FOR MEDICAL DEVICES

FIELD OF THE INVENTION

The invention relates to a coating for a medical device. The invention further relates to a medical device comprising the coating, and to uses and methods involving the coating or the medical device comprising the coating. The invention also relates to a method of manufacturing the coating and to a kit for coating a medical device.

BACKGROUND

The formation of blood clots within an organ or a tissue can present a potentially life-threatening condition. When using a medical device, blood may come into contact with the foreign surfaces of the device, which may trigger the formation of a blood clot. Consequently, patients may be given an anticoagulant prior to the use of the medical device to suppress blood coagulation and the formation of blood clots. There are, however, considerable side effects associated with the administration of an anticoagulant that have to be taken into account. It may not be safe to administer such anticoagulants to some patients.

Some medical devices, such as stents, have been coated with heparin, which is an anticoagulant that prevents the formation of blood clots. Heparin is a glycosaminoglycan. It is can be difficult to coat onto a medical device and it is relatively expensive. The use of heparin is also associated with several side effects, which include bleeding, severe pain (e.g. at the injection site), nausea and unusual tiredness. There are also serious side effects associated with the use of heparin, such as heparin-induced thrombocytopenia. Heparin is contraindicated for several conditions, which include brain operation, operation on the spine, eye surgery, haemophilia, a deficiency of anti-clotting agents, significant uncontrolled high blood pressure, subacute infection of heart valve, a haemorrhage in the brain, bulge and tear of the aorta blood vessel wall, stomach or intestinal ulcer, ulcerative colitis, an inflammatory condition of the intestines, diverticulitis, severe liver disease, biliary and gallbladder problem, osteoporosis, and chronic kidney disease, which is stage 4 (severe) or stage 5 (failure).

Other types of coating have been applied to medical devices. These coatings typically comprise a multifunctional polymerizable compound. A problem with such coatings is that they can show poor coating performance and can degrade within a relatively short time. When the coatings lack mechanical robustness, the by-products of degradation can leach into the patient, which may be undesirable for certain types of coating.

SUMMARY OF THE INVENTION

The invention provides a coating for a medical device comprising: a surface layer; and optionally a base layer; wherein the surface layer comprises a polymer chain attached or bonded to an anti-clotting group.

The coating of the invention is non-thrombogenic and is hemocompatible. The coating has a prophylactic effect in that it can prevent or inhibit the formation of blood clots, which, in turn, prevents or inhibits the onset, progression or recurrence of diseases and conditions associated with blood clots.

The inventors have discovered a polymeric material (e.g. polymer chain) that has advantageous properties for use as a coating for a medical device, particularly when it is attached to anti-clotting groups. The anti-clotting groups may also be referred to as hemocompatible groups (i.e. the term "anti-clotting group" is synonymous with "hemocompatible group"). The hemocompatible groups contribute to the overall hemocompatibility of the coating.

Typically, the anti-clotting group is a sulfonic acid group, a sulfonamide group, a sulfamic acid group, a hydrogen sulfate group or a conjugate base thereof. Without wishing to be bound by theory, it is believed that when these groups in the coating are ionised, then the negatively charged conjugate base (e.g. sulfonate group etc) repels the adhesion of platelets, thereby inhibiting or preventing the formation of a blood clot on a surface of the coating.

The invention also provides a medical device. The medical device has a surface coated with a coating of the invention. The presence of the coating on a surface of the medical device prevents or inhibits the formation of blood clots on the device when it is used.

The invention further provides a polymeric compound. The polymeric compound is represented by formula (C-2):

(C-2)

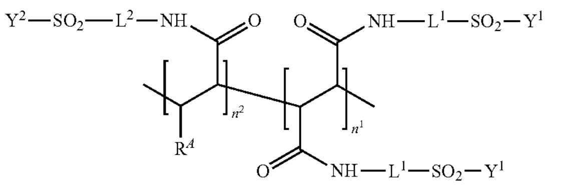

wherein:

each $Y^1$ is selected from $O^-$, OH, $NH^-$, and $NH_2$, preferably selected from $O^-$ and OH;

$Y^2$ is selected from $O^-$ and OH;

each $L^1$ is $C_{2-5}$ alkylene;

$L^2$ is $C_{2-5}$ alkylene;

$R^4$ is selected from H and $C_{1-6}$ alkyl;

$n^1$ is an integer; and $n^2$ is an integer.

The invention also provides a method of manufacturing a coating for a medical device. The method may comprise attaching or bonding a compound comprising an anti-clotting agent to a polymer using a coupling agent. The anti-clotting agent may also be referred to as a hemocompatibility agent (i.e. the term "anti-clotting agent" is synonymous with the term "hemocompatibility agent"). The method may produce a polymer compound, such as represented by formula (C-2) above.

The invention may further provide comprise a method of coating a surface of a medical device. The method may comprise: optionally applying a base layer to a surface of the medical device, and applying a coating to a surface of the medical device.

A further aspect of the invention relates to a kit for coating a medical device. The kit comprises: (a) a polymer, (b) compound comprising an anti-clotting group, (c) a coupling agent, and optionally (d) a coating for forming the base layer.

The invention further relates to uses of the coating and the medical device.

The coating of the invention or the medical device of the invention can be used in the treatment of the human or animal body by surgery or therapy and/or in a diagnostic method practised on the human or animal body. The diagnostic method practised on the human or animal body is typically an in vivo diagnostic method.

The coating of the invention or the medical device of the invention is for use in reducing or preventing the clotting of blood.

The invention also provides a method of reducing or preventing the clotting of blood. The method comprises contacting a medical device of the invention with blood.

An aspect of the method of the invention may be an in vitro method of reducing or preventing the clotting of blood, such as when processing the blood. The method may comprise contacting the medical device with blood, wherein the blood has been removed from a human or animal body. The blood may be contacted with the medical device to process the blood. The processed blood may not be returned to the human or animal body, preferably the human or animal body from which the blood was removed.

Another aspect of the method of the invention is a method of reducing or preventing the clotting of blood in a diagnostic procedure. The method may comprise contacting the medical device with blood to obtain diagnostic information.

BRIEF DESCRIPTION OF THE DRAWINGS

The invention is further described hereinafter with reference to the accompanying drawings.

DEFINITIONS

Figure 1:
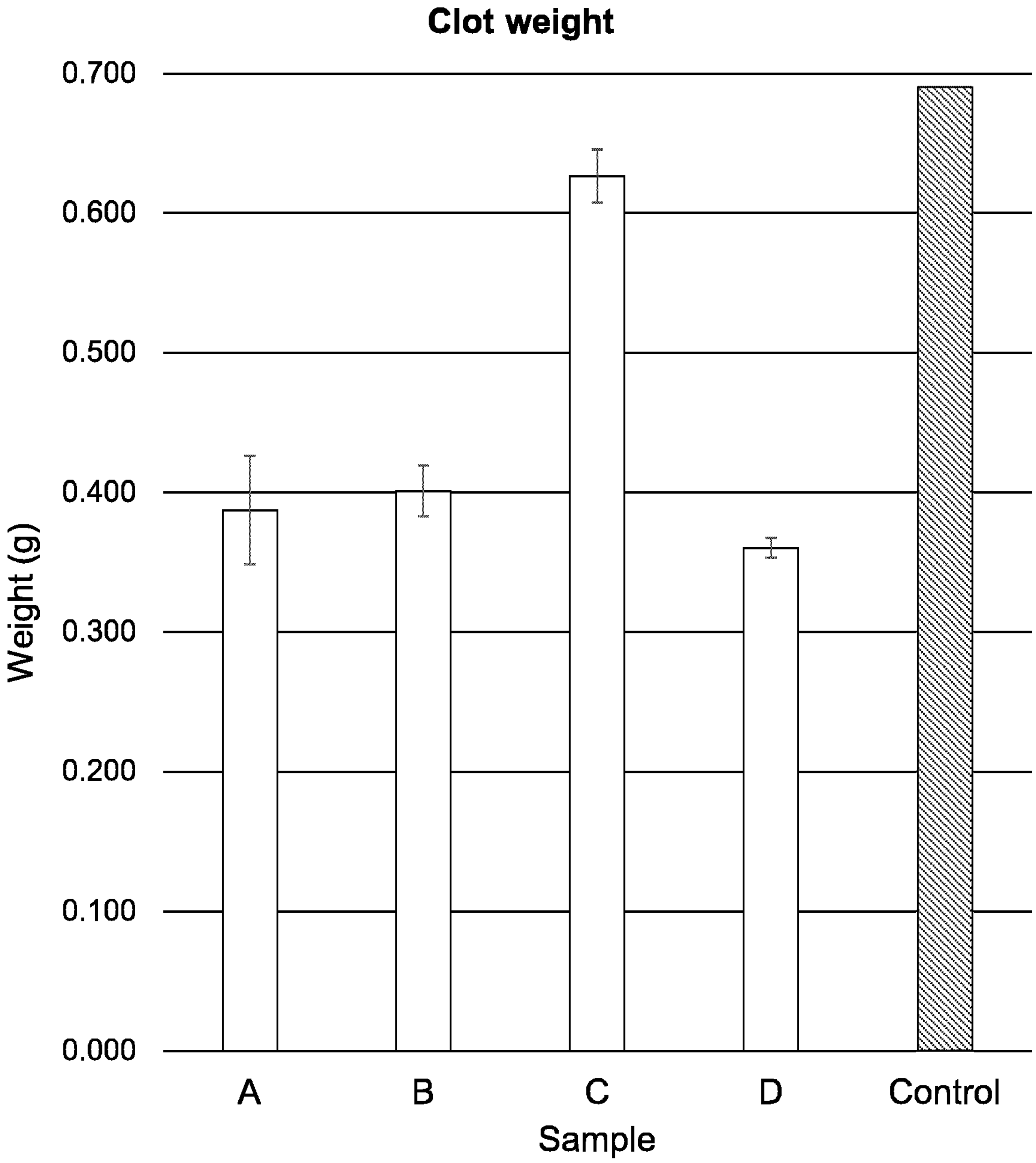
FIG. 1 is a histogram showing the clot weights of samples obtained from a whole blood assay experiment.

The term "biocompatible" as used herein, particularly in the context of the coating or its constituents, refers to the ability of a medical device or a material to perform with an appropriate host response in a specific application (e.g. as set out in ISO 10993-1 (2018)). The definition of "biocompatibility", its associated terms and tests for its evaluation in ISO 10993-1 (2018) are incorporated herein by reference. In general terms, biocompatibility refers to the ability of a medical device or a material to perform its desired function with respect to a medical therapy, without eliciting any undesirable local or systemic effects in the recipient or beneficiary of that therapy, but generating the most appropriate beneficial cellular or tissue response in that specific situation, and optimising the clinically relevant performance of that therapy.

For convenience, the term "sulfonic group" is used herein. In general, the term "sulfonic group" is a sulfonic acid group ($—SO_3H$) or a sulfonate group ($—SO_3^-$). The plural term "sulfonic groups" embraces sulfonic acid groups ($—SO_3H$), sulfonate groups ($—SO_3^-$) or a combination of at least one sulfonic acid group ($—SO_3H$) and at least one sulfonate group ($—SO_3^-$), unless the context indicates otherwise. It should be appreciated that in certain environments, such as physiological environments, the sulfonic acid group ($—SO_3H$) may dissociate into a sulfonate group ($—SO_3^-$) or an equilibrium may exist therebetween.

In general, the term "sulfonic group precursor" as used herein refers to a precursor group that can be hydrolysed to a sulfonic group as defined herein. The precursor group may be a sulfonamide group (e.g. $—SO_2NH_2$, $—SO_2NHR^a$ or $—SO_2NR^aR^b$) or a sulfonate ester group ($—SO_3R^a$). $R^a$ and $R^b$ may each independently be selected from $C_1$-$C_6$ alkyl, phenyl and benzyl.

The term "alkyl" as used herein refers to a straight or branched hydrocarbon chain radical consisting of carbon and hydrogen atoms, and containing no unsaturation. A "$C_{1-6}$ alkyl" group contains one to six carbon atoms. Unless stated otherwise specifically in the specification, an alkyl group is unsubstituted or may be substituted by one or more substituents selected from hydroxy, $C_{1-6}$ alkoxy and halo, which is preferably fluoro. It is preferred that the alkyl group is unsubstituted.

The term "alkene" as used herein refers to a straight or branched hydrocarbon chain radical group consisting of carbon and hydrogen atoms, and containing at least one carbon-carbon double bond.

The term "alkoxy" as used herein refers to a radical bonded through an oxygen atom of the formula —O-alkyl, where the alkyl group is defined above. The term "aryloxy"

as used herein refers to a radical bonded through an oxygen atom of the formula —O-aryl, where the aryl group is defined above.

The term "aryl" as used herein refers to a radical derived from an aromatic monocyclic or polycyclic hydrocarbon ring system by removing a hydrogen atom from a ring carbon atom. The aromatic monocyclic or polycyclic hydrocarbon ring system contains only hydrogen atoms and carbon atoms, where at least one of the rings in the ring system is fully unsaturated (i.e. it contains a cyclic, delocalized [4n+2] π-electron system in accordance with the Hückel theory). The ring system from which aryl groups may be derived include, for example, benzene, indane, indene, tetralin and naphthalene.

The term "aryl-alkyl" as used herein refers to a radical bonded to an alkyl group, such as defined above, which alkyl group is further substituted by (or bonded to) an aryl group as defined above. Examples of aryl-alkyl groups include benzyl ($PhCH_2$—) and phenylethyl.

The term "alkylene" as used herein refers to a straight or branched divalent hydrocarbon chain, which consists of carbon and hydrogen atoms, and contains no unsaturation. Examples of preferred alkylene groups include $—CH_2—$, $—CH_2—CH_2—$, $—CH_2—CH_2—CH_2—$, $—CH(CH_3)—$, and $—C(CH_3)_2—CH_2—$. A "$C_{1-10}$ alkylene" group contains one to ten carbon atoms. It is preferred that the alkylene is straight (e.g. unbranched).

The term "alkenylene" as used herein refers to a straight or branched divalent hydrocarbon chain, which consists of carbon and hydrogen atoms, and contains at least one double bond. The alkene group may have a cis or a trans arrangement. Examples of alkenylene groups include $—CH{=}CH—$, $—CH_2—CH{=}CH—$, $—C(CH_3){=}CH—CH_2—$, $—CH_2—C(CH_3){=}CH—CH_2—$, and $—CH_2—CH{=}C{=}CH—CH_2—$. A "$C_{2-10}$ alkenylene" group contains two to ten carbon atoms. When the alkenylene contains more than one double bond, then the double bonds may be conjugated or non-conjugated. It is preferred that the alkenylene group does not comprise an allene group. More preferably, it is preferred that the alkenylene group comprises a single double bond.

The term "alkynylene" as used herein refers to a straight or branched divalent hydrocarbon chain, which consists of carbon and hydrogen atoms, and contains at least triple double bond. Examples of alkylene groups include $—C{\equiv}C—$, $—CH_2—C{\equiv}C—$, $—CH(CH_3)—C{\equiv}C—CH_2—$, and $—CH_2—C{\equiv}C—C{\equiv}C\ C(CH_3){=}CH—CH_2—$. A "$C_{2-10}$ alkynylene" group contains two to ten carbon atoms. When the alkynylene contains more than one triple bond, then the triple bonds may be conjugated or non-conjugated. Preferably, an alkynylene group does not include a double bond (e.g. carbon-carbon double bond). More preferably, the alkynylene group comprises a single triple bond.

The term "phenylene" as used herein refers to a divalent radical derived from benzene (e.g. $—C_6H_4—$). The divalent radical (e.g. a di-substituted benzene ring) may have an ortho arrangement of substituents, a meta arrangement of substituents or a para arrangement of substituents.

Unless stated otherwise specifically in the specification, each group mentioned above (e.g. alkyl, alkene, alkoxy, aryl, aryl-alkyl, alkylene, alkenylene, alkynylene, phenylene) is unsubstituted.

DETAILED DESCRIPTION

The invention provides a coating for a medical device. The coating reduces or prevents the clotting of blood. The coating is typically an antithrombotic coating, such as an anticoagulant coating and/or an antiplatelet coating, preferably an antiplatelet coating. The coating is typically a hemocompatible coating.

Any reference to "blood" as used herein generally refers to the blood of a human or a non-human animal, such as a mammalian animal. The invention can be used in veterinary applications. The term "blood" preferably refers to the blood of a human.

Typically, the coating is biocompatible, preferably biocompatible and/or hemocompatible.

The coating comprises, or may consist essentially of, a surface layer. The surface layer is the topmost layer of the coating. Thus, the surface layer may be an outer surface layer of the coating or a coated medical device. In use, the surface layer of the coating comes into contact with blood.

The surface layer or the coating (e.g. as a whole) may be in the form of a gel, preferably a hydrogel. The hydrogel may provide the medical device with a lubricious surface. When the surface layer or the coating is in the form of a gel, then it can be easily applied to the medical device.

The surface layer comprises, or may consist essentially of, a polymer chain attached or bonded (e.g. covalently bonded) to an anti-clotting group.

The anti-clotting group is typically selected from a sulfonic acid group, a sulfonamide group, a sulfamic acid group, a hydrogen sulfate group and a conjugate base thereof. The structures of each group is shown below, where the squiggly line indicating the point of attachment of the group to the polymer chain, either directly or indirectly.

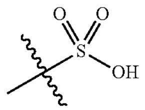
sulfonic acid

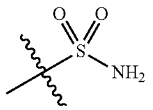
sulfonamide

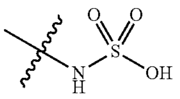
sulfamic acid

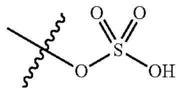
hydrogen sulfate

In general, it is preferred that the anti-clotting group is selected from a sulfonic acid group, a sulfamic acid group, a hydrogen sulfate group and a conjugate base thereof.

The conjugate base of each group is shown below. The conjugate base of each group refers to a sulfonate group, sulfonamide anion group, a sulfamate group or a sulfate group respectively.

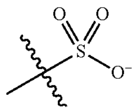
sulfonate group

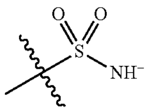
sulfonamide anion group

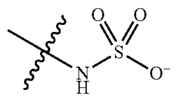
sulfamate group

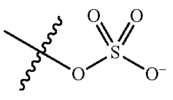
sulfate group

In general, it is preferred that the anti-clotting group is a conjugate base of the sulfonic acid group, the sulfamic acid group or the hydrogen sulfate group. Thus, the anti-clotting group is preferably a sulfonate group, a sulfamate group or a sulfate group, such as shown above.

It is preferred that the polymer chain is attached or bonded to a plurality of anti-clotting groups. Each anti-clotting group of the plurality of anti-clotting groups is typically selected from a sulfonic acid group, a sulfamic acid group, a hydrogen sulfate group and a conjugate base thereof, as defined above.

Generally, the anti-clotting group is attached or bonded to the polymer chain by a linker group. In principle, any linker group may be used to connect the polymer chain to the anti-clotting group. However, certain linker groups may provide, or contribute to, the advantageous properties of the coating.

The linker group covalently bonds at least one anti-clotting group to the polymer chain. Thus, the linker group may have a first end that is covalently bonded to the polymer chain and a second end that is covalently bonded to at least one anti-clotting group.

A single anti-clotting group may be attached or bonded to the polymer chain by the linker group (e.g. a single linker group). Alternatively, a plurality of anti-clotting groups, such as two or three anti-clotting groups, may be bonded to the polymer chain by the linker group (e.g. a single linker group).

The polymer chain may be a linear polymer chain or a branched polymer chain. It is preferred that the polymer chain is a linear polymer chain.

In general, the surface layer is biocompatible. It is further preferred that the polymer chain is biocompatible.

The polymer chain typically has a number average (e.g. mean) molecular weight ($M_n$) of at least 300 g/mol, such as 300 to 50,000 g/mol, preferably 500 to 30,000 g/mol, more preferably 1,000 to 10,000 g/mol. The number average (e.g. mean) molecular weight ($M_n$) can be determined by light scattering.

Typically, the anti-clotting group is a sulfonic acid group or a sulfonate group. It is preferred that each anti-clotting group of the plurality of anti-clotting groups is a sulfonic acid group or a sulfonate group.

As mentioned above, the term "sulfonic group" is used herein as a shorthand to refer to a sulfonic acid group ($—SO_3H$) or a sulfonate group ($—SO_3^-$). The plural term "sulfonic groups" as used herein refers to sulfonic acid groups ($—SO_3H$), sulfonate groups ($—SO_3^-$) or a combination of at least one sulfonic acid group ($—SO_3H$) and at least one sulfonate group ($—SO_3^-$), unless the context indicates otherwise.

Accordingly, the surface layer comprises, or may consist essentially of, a polymer chain attached or bonded to a plurality of sulfonic groups.

In a first aspect of the invention, the anti-clotting groups, particularly the sulfonic groups, can be attached to the polymer chain after it has been formed by polymerisation, instead of polymerising monomers that include anti-clotting groups. In this context, the polymer chain attached or bonded to an anti-clotting group or a plurality of anti-clotting groups may be referred to herein as a polymer chain linked or coupled to an anti-clotting group or a plurality of anti-clotting groups, particularly when the or each anti-clotting group is a sulfonic group.

Each sulfonic group may be linked or coupled to the polymer chain by a linker group.

It is believed that the linker group should be relatively short (e.g. 1 to 3 atoms in length) to ensure that the surface of the coating presents a high negative charge density to platelets. When longer linker groups are used, then it is possible for the surface of the coating to have a disordered arrangement of anti-clotting groups, particularly sulfonic groups, due to the conformational flexibility of the linker group. This can reduce the negative charge density provided by the surface of the coating.

In general, it is preferred that the linker group is biocompatible.

The polymer chain may include a repeating unit comprising a moiety as represented by formula (A-0):

(A-0)

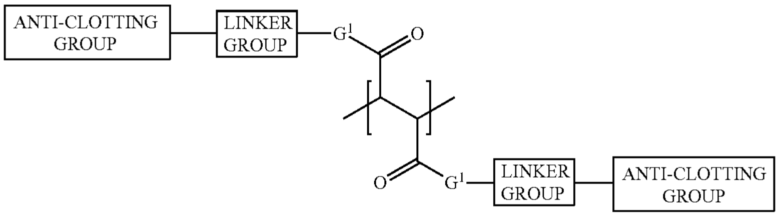

wherein:

each $G^1$ is the same or different and is independently selected from O, NH, and $NR^{1A}$; and each $R^{1A}$ is independently selected from $C_{1-6}$ alkyl, $C_{6-10}$ aryl and $C_{6-10}$ aryl-$C_{1-6}$ alkyl.

It is preferred that each $G^1$ is the same.

The polymer chain may include a repeating unit represented by formula (A-1) below.

(A-1)

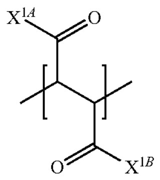

In formula (A-1) above:

$X^{1A}$ is selected from $O^-$, OH, $OR^{1A}$, $NH_2$, $NHR^{1A}$ and $A^{1A}$;

$X^{1B}$ is selected from $O^-$, OH, $OR^{1B}$, $NH_2$, $NHR^{1B}$ and $A^{1B}$;

each of $R^{1A}$ and $R^{1B}$ is independently selected from $C_{1-6}$ alkyl, $C_{6-10}$ aryl and $C_{6-10}$ aryl-$C_{1-6}$ alkyl;

each of $A^{1A}$ and $A^{1B}$ is independently represented by formula (S-1):

$$—Z^1\text{-}L^1\text{-}SO_2—Y^1 \quad \text{(S-1)}$$

wherein:

$Z^1$ is selected from O, NH and $NR^1$;

$R^1$ is selected from $C_{1-6}$ alkyl, $C_{6-10}$ aryl and $C_{6-10}$ aryl-$C_{1-6}$ alkyl;

$Y^1$ is selected from $O^-$ and OH;

$L^1$ is represented by formula (L-1):

$$—P^1\text{-}Q^1\text{-}W^1— \quad \text{(L-1)}$$

wherein:

$P^1$ is selected from a single bond, $C_{1-10}$ alkylene, $C_{2-10}$ alkenylene, $C_{2-10}$ alkynylene and phenylene;

$Q^1$ is selected from a single bond, O, NH, $NR^{1C}$ and phenylene;

$W^1$ is selected from a single bond, $C_{1-10}$ alkylene, $C_{2-10}$ alkenylene, $C_{2-10}$ alkynylene and phenylene; and $R^{1C}$ is selected from $C_{1-6}$ alkyl, $C_{6-10}$ aryl and $C_{6-10}$ aryl-$C_{1-6}$ alkyl.

When formula (L-1) is combined with formula (S-1), then each of $A^{1A}$ and $A^{1B}$ is independently represented by formula (S-1A):

$$—Z^1—P^1\text{-}Q^1\text{-}W^1—SO_2—Y^1 \quad \text{(S-1A).}$$

The repeating unit represented by formula (A-1) above may, for example, be obtainable from a maleic acid monomer or a maleimide monomer.

In formula (A-1), the moiety -$L^1$- represents the linker group.

The polymer chain that is linked or coupled to a plurality of sulfonic groups may include a repeating unit represented by any one of formulae (A-1) to (A-3) described herein.

In the polymer chain, each unit in the repeating unit represented by formula (A-1) may be the same or different.

Typically, the surface layer comprises a plurality of polymeric compounds (e.g. a distribution), wherein each polymer compound comprises a polymer chain including a repeating unit as represented by any one of formulae (A-1) to (A-3) described herein.

The linker group and sulfonic group are attached to the polymer chain after polymerisation of an appropriate monomer, such as maleic acid or maleimide. The linker group and sulfonic group are introduced into the repeating unit, such as by a reaction at the carbonyl group. This can be achieved by reacting a compound comprising an anti-clotting agent with a polymer using a coupling agent, as described below. It is possible that some of the carbonyl groups do not undergo a reaction (i.e. there is not 100% conversion) to include the linker and sulfonic groups. When this happens, then (a) $X^{1A}$ may be $O^-$, OH, $OR^{1A}$, $NH_2$ or $NHR^{1A}$ and/or (b) $X^{1B}$ may be $O^-$, OH, $OR^{1B}$, $NH_2$ or $NHR^{1B}$.

In general, such as when the surface layer comprises a plurality of polymeric compounds, it is preferred that at least 90% of the units represented by formula (A-1) include $A^{1A}$ and/or $A^{1B}$ as defined above (i.e. $X^{1A}$ is $A^{1A}$ and/or $X^{1B}$ is $A^{1B}$), more preferably at least 95% of the units represented by formula (A-1) include $A^{1A}$ and/or $A^{1B}$, and even more preferably at least 99% of the units represented by formula (A-1) include $A^{1A}$ and/or $A^{1B}$.

Typically, each unit in the repeating unit represented by formula (A-1) includes at least one of $A^{1A}$ or $A^{1B}$ as defined above (i.e. $X^{1A}$ is $A^{1A}$ or $X^{1B}$ is $A^{1B}$), more preferably each unit in the repeating unit represented by formula (A-1) includes $A^{1A}$ and $A^{1B}$ as defined above (i.e. $X^{1A}$ is $A^{1A}$ and $X^{1B}$ is $A^{1B}$). Thus, both $X^{1A}$ is $A^{1A}$ and $X^{1B}$ is $A^{1B}$.

It is preferred that each unit in the repeating unit represented by formula (A-1) is the same.

The polymer chain may include a repeating unit represented by formula (A-2) below.

(A-2)

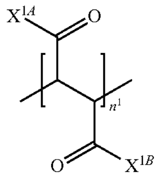

In formula (A-2), each of $X^{1A}$, $X^{1B}$, $R^{1A}$, $R^{1B}$, $A^{1A}$, $A^{1B}$, $Z^1$, $R^1$, $Y^1$, $L^1$, $P^1$, $Q^1$, $W^1$ and $R^{1C}$ is as defined above, and wherein at least one of $X^{1A}$ is $A^{1A}$ or $X^{1B}$ is $A^{1B}$, and $n^1$ is an integer.

In formula (A-1) or formula (A-2), it is preferred that $X^{1A}$ is selected from $O^-$, OH, $OR^{1A}$ and $A^{1A}$; and $X^{1B}$ is selected from $O^-$, OH, $OR^{1B}$ and $A^{1B}$. More preferably, $X^{1A}$ is selected from $O^-$, OH and $A^{1A}$; and $X^{1B}$ is selected from $O^-$, OH, and $A^{1B}$. Even more preferably, $X^{1A}$ is $A^{1A}$; and $X^{1B}$ is $A^{1B}$, such as represented in formula (A-3) below.

(A-3)

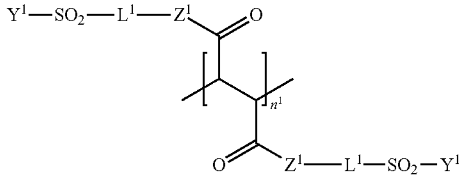

In formula (A-1) or formula (A-2), when $X^{1A}$ is $OR^{1A}$ or $NHR^{1A}$, then it is preferred that $R^{1A}$ is $C_{1-6}$ alkyl, particularly methyl or ethyl. Alternatively or additionally, when $X^{1B}$ is $OR^{1B}$ or $NHR^{1B}$, then it is preferred that $R^{1B}$ is $C_{1-6}$ alkyl, particularly methyl or ethyl.

In formula (A-1) or formula (A-2), $A^{1A}$ and $A^{1B}$ may be the same or different. In general, it is preferred that $A^{1A}$ and $A^{1B}$ are the same.

In formulae (A-1) to (A-3) above, when $Z^1$ is $NR^1$, then it is preferred that $R^1$ is $C_{1-6}$ alkyl, particularly methyl or ethyl.

Typically, each $Z^1$, in the formulae (A-1) to (A-3) above, is preferably selected from O and NH. Each $Z^1$ may be O. More preferably, each $Z^1$ is NH. When $Z^1$ is O or NH, then the linker group is attached to the polymer chain by an ester or amide group, which is typically a biocompatible group. Amide groups, in particular, have biocompatibility because, for example, they are present in peptides.

Generally, in formulae (A-1) to (A-3), each $L^1$ may be the same or different. It is preferred that each $L^1$ is the same.

Each $P^1$ is typically selected from a single bond, $C_{1-10}$ alkylene and phenylene; and each $W^1$ may be selected from a single bond, $C_{1-10}$ alkylene and phenylene. More preferably, each $P^1$ may be selected from a single bond and $C_{1-10}$ alkylene; and each $W^1$ may be selected from a single bond and $C_{1-10}$ alkylene.

Alternatively, each $P^1$ is selected from $C_{1-10}$ alkylene, $C_{2-10}$ alkenylene and $C_{2-10}$ alkynylene; each $Q^1$ is selected from O, NH and $NR^{1C}$ and each $W^1$ is a single bond. More preferably each $Q^1$ is selected from O and NH. In this arrangement, the anti-clotting group is a sulfamate group, a sulfate group or a conjugate base thereof.

Typically, for each $L^1$ it is preferred that at least one of $P^1$, $Q^1$ and $W^1$ is not a single bond.

When $Q^1$ is O, it is generally preferred that $P^1$ is not a single bond. More preferably, when $Q^1$ is O, it is preferred that $P^1$ is $C_{1-10}$ alkylene, more preferably $P^1$ is $C_{2-4}$ alkylene.

When $Q^1$ is O and $P^1$ is not a single bond, it may be preferable that $W^1$ is not a single bond. More preferably, when $Q^1$ is O, it is preferred that $P^1$ is $C_{1-10}$ alkylene and W is $C_{1-10}$ alkylene, more preferably $P^1$ is $C_{2-4}$ alkylene and $W^1$ is $C_{2-4}$ alkylene.

When $Q^1$ is phenylene, it is generally preferred that $P^1$ is a single bond or $C_{1-10}$ alkylene and $W^1$ is a single bond or $C_{1-10}$ alkylene. More preferably, when $Q^1$ is phenylene, it is preferred that $P^1$ is a single bond or $C_{1-3}$ alkylene and $W^1$ is a single bond or $C_{1-3}$ alkylene.

In general, it is preferred that each $P^1$ is selected from $C_{1-10}$ alkylene, $C_{2-10}$ alkenylene and $C_{2-10}$ alkynylene; each $Q^1$ is a single bond and each $W^1$ is a single bond. More preferably, each $P^1$ is $C_{1-10}$ alkylene, particularly $C_{2-6}$ alkylene, such as $C_{2-5}$ alkylene. Even more preferably each $P^1$ is butylene, propylene or ethylene, preferably ethylene. When $P^1$ is ethylene and both $Q^1$ and $W^1$ are single bonds, then the moiety represented by (S-1) can be formed from taurine. Taurine is naturally found in the human body and can be formed if degradation of the polymeric compound occurs.

Typically, the integer represented $n^1$ is at least 5, preferably at least 10. For example, $n^1$ may be from 5 to 500, such as from 10 to 300, more preferably from 15 to 100.

The polymer chain may be anionic, such as when $X^{1A}$, $X^{1B}$ or $Y^1$ is $O^-$. When the polymer chain is anionic, then $Na^+$ or $K^+$ may be present as a counter cation.

For convenience, the repeating unit represented by formulae (A-0) to (A-3) is referred to herein using the label the "first repeating unit". The label "first" in this context is used to distinguish this repeating unit from other types of repeating unit. It does not require the "first repeating unit" to be present when reference is made to a "second repeating unit", a "third repeating unit" etc.

In addition to or as an alternative to the repeating unit represented by formulae (A-0) to (A-3) above, the polymer chain may include a repeating unit comprising a moiety as represented by formula (B-0):

(B-0)

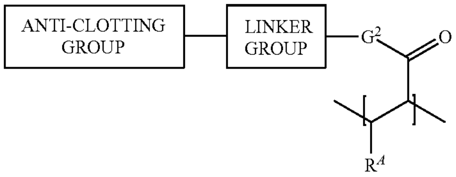

wherein:

$G^2$ is selected from O, NH, and $NR^{2A}$;

$R^{2A}$ is independently selected from $C_{1-6}$ alkyl, $C_{6-10}$ aryl and $C_{6-10}$ aryl-$C_{1-6}$ alkyl; and $R^A$ is selected from H and $C_{1-6}$ alkyl.

The polymer chain may include a repeating unit represented by formula (B-1).

(B-1)

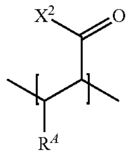

In formula (B-1) above:

$R^A$ is selected from H and $C_{1-6}$ alkyl;

$X^2$ is selected from $O^-$, OH, $OR^{2A}$, $NH_2$, $NHR^{2A}$ and $A^2$;

$R^{2A}$ is selected from $C_{1-6}$ alkyl, $C_{6-10}$ aryl and $C_{6-10}$ aryl-$C_{1-6}$ alkyl;

$A^2$ is represented by formula (S-2):

$$—Z^2\text{-}L^2\text{-}SO_2—Y^2 \quad (S\text{-}2)$$

wherein:

$Z^2$ is selected from O, NH and $NR^2$;

$R^2$ is selected from $C_{1-6}$ alkyl, $C_{6-10}$ aryl and $C_{6-10}$ aryl-$C_{1-6}$ alkyl;

$Y^2$ is selected from $O^-$ and OH;

$L^2$ is represented by formula (L-2):

$$—P^2\text{-}Q^2\text{-}W^2— \quad (L\text{-}2)$$

wherein:

$P^2$ is selected from a single bond, $C_{1-10}$ alkylene, $C_{2-10}$ alkenylene, $C_{2-10}$ alkynylene and phenylene;

$Q^2$ is selected from a single bond, O, NH, $NR^{2C}$ and phenylene;

$W^2$ is selected from a single bond, $C_{1-10}$ alkylene, $C_{2-10}$ alkenylene, $C_{2-10}$ alkynylene and phenylene; and $R^{2C}$ is selected from $C_{1-6}$ alkyl, $C_{6-10}$ aryl and $C_{6-10}$ aryl-$C_{1-6}$ alkyl.

When formula (L-2) is combined with formula (S-2), then $A^2$ is represented by formula (S-2A):

$$—Z^2—P^2\text{-}Q^2\text{-}W^2—SO_2—Y^2 \quad (S\text{-}2A).$$

The repeating unit represented by formula (B-1) above may, for example, be obtainable from an acrylic acid monomer, a methacrylic acid monomer, an acrylamide monomer or a methacrylamide monomer.

In formula (B-1), the moiety -$L^2$- represents the linker group.

The polymer chain that is linked or coupled to a plurality of sulfonic groups may include a repeating unit represented by any one of formulae (B-1) to (B-3) described herein.

In the polymer chain, each unit in the repeating unit represented by formula (B-1) may be the same or different.

Typically, the surface layer comprises a plurality of polymeric compounds (e.g. a distribution), wherein each polymer compound comprises a polymer chain including a repeating unit as represented by any one of formulae (B-1) to (B-3) described herein.

The linker group and sulfonic group are attached to the polymer chain after polymerisation of an appropriate monomer, such as acrylic acid or methacrylic acid. The linker group and sulfonic group are introduced into the repeating unit, such as by a reaction at the carbonyl group. It is possible that some of the carbonyl groups do not undergo a reaction (i.e. there is not 100% conversion) to include the linker and sulfonic groups. When this happens, then $X^2$ may be $O^-$, OH, $OR^{2A}$, $NH_2$ or $NHR^{2A}$.

In general, such as when the surface layer comprises a plurality of polymeric compounds, it is preferred that at least 90% of the units represented by formula (B-1) include $A^2$ as defined above (i.e. $X^2$ is $A^2$), more preferably at least 95% of the units represented by formula (B-1) include $A^2$, and even more preferably at least 99% of the units represented by formula (B-1) include $A^2$.

Typically, each unit in the repeating unit represented by formula (B-1) includes $A^2$ (i.e. $X^2$ is $A^2$).

It is preferred that each unit in the repeating unit represented by formula (B-1) is the same.

The polymer chain may include a repeating unit represented by formula (B-2) below.

(B-2)

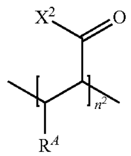

In formula (B-2), each of $R^A$, $X^2$, $R^{2A}$, $A^2$, $Z^2$, $R^2$, $Y^2$, $L^2$, $P^2$, $Q^2$, $W^2$ and $R^{2C}$ is as defined above, and wherein $n^2$ is an integer.

In formula (B-1) or formula (B-2), it is preferred that $X^2$ is selected from $O^-$, OH, $OR^{2A}$ and $A^2$. More preferably, $X^2$ is selected from $O^-$, OH and $A^2$. Even more preferably, $X^2$ is $A^2$, such as represented in formula (B-3) below.

(B-3)

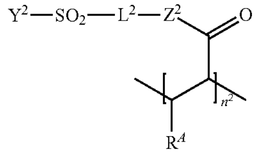

Typically, in formulae (B-1) to (B-3) above, $R^A$ is selected from H and $C_{1-3}$ alkyl, preferably $R^A$ is selected from H and methyl. Even more preferably, $R^A$ is H.

In formula (B-1) or formula (B-2), when $X^2$ is $OR^{2A}$ or $NHR^{2A}$, then it is preferred that $R^{2A}$ is $C_{1-6}$ alkyl, particularly methyl or ethyl.

In formulae (B-1) to (B-3) above, when $Z^2$ is $NR^2$, then it is preferred that $R^2$ is $C_{1-6}$ alkyl, particularly methyl or ethyl.

Typically, $Z^2$, in the formulae (B-1) to (B-3) above, is preferably selected from O and NH. $Z^2$ may be O. More preferably, $Z^2$ is NH. When $Z^2$ is O or NH, then the linker group is attached to the polymer chain by an ester or amide group, which is typically a biocompatible group. Amide groups, in particular, are biocompatible because they are present in peptides.

$P^2$ is typically selected from a single bond, $C_{1-10}$ alkylene and phenylene; and $W^2$ may be selected from a single bond, $C_{1-10}$ alkylene and phenylene. More preferably, $P^2$ may be selected from a single bond and $C_{1-10}$ alkylene; and $W^2$ may be selected from a single bond and $C_{1-10}$ alkylene.

Alternatively, $P^2$ is selected from $C_{1-10}$ alkylene, $C_{2-10}$ alkenylene and $C_{2-10}$ alkynylene; $Q^2$ is selected from O, NH and $NR^{2C}$ and $W^2$ is a single bond. More preferably $Q^2$ is selected from O and NH. In this arrangement, the anti-clotting group is a sulfamate group, a sulfate group or a conjugate base thereof.

Typically, for $L^2$ it is preferred that at least one of $P^2$, $Q^2$ and $W^2$ is not a single bond.

When $Q^2$ is O, it is generally preferred that $P^2$ is not a single bond. More preferably, when $Q^2$ is O, it is preferred that $P^2$ is $C_{1-10}$ alkylene, more preferably $P^2$ is $C_{2-4}$ alkylene.

When $Q^2$ is O and $P^2$ is not a single bond, it may be preferable that $W^2$ is not a single bond. More preferably, when $Q^2$ is O, it is preferred that $P^2$ is $C_{1-10}$ alkylene and $W^2$ is $C_{1-10}$ alkylene, more preferably $P^2$ is $C_{2-4}$ alkylene and $W^2$ is $C_{2-4}$ alkylene.

When $Q^2$ is phenylene, it is generally preferred that $P^2$ is a single bond or $C_{1-10}$ alkylene and $W^2$ is a single bond or $C_{1-10}$ alkylene. More preferably, when $Q^2$ is phenylene, it is preferred that $P^2$ is a single bond or $C_{1-3}$ alkylene and $W^2$ is a single bond or $C_{1-3}$ alkylene.

In general, it is preferred that $P^2$ is selected from $C_{1-10}$ alkylene, $C_{2-10}$ alkenylene and $C_{2-10}$ alkynylene; $Q^2$ is a single bond and $W^2$ is a single bond. More preferably, $P^2$ is $C_{1-10}$ alkylene, particularly $C_{2-6}$ alkylene, such as $C_{2-5}$ alkylene. Even more preferably $P^2$ is butylene, propylene or ethylene, preferably ethylene. When $P^2$ is ethylene and both $Q^2$ and $W^2$ are single bonds, then the moiety represented by (S-2) can be formed from taurine. As mentioned above, taurine can be formed if degradation of the polymeric compound occurs.

Typically, the integer represented by $n^2$ is at least 5, preferably at least 10. For example, $n^2$ may be from 5 to 500, such as from 10 to 300, more preferably from 15 to 100.

The polymer chain may be anionic, such as when $X^2$ or $Y^2$ is $O^-$. When the polymer chain is anionic, then $Na^+$ or $K^+$ may be present as a counter cation.

For convenience, the repeating unit represented by formulae (B-0) to (B-3) is referred to herein using the label the "second repeating unit". The label "second" in this context is used to distinguish this repeating unit from the "first repeating unit". As mentioned above, this label does not require that the "first repeating unit" must be present in addition to the "second repeating unit".

The polymer chain that is linked or coupled to a plurality of sulfonic groups may be a copolymer.

The copolymer may be an alternating copolymer comprising a first repeating unit represented by any one of formulae (A-0) to (A-3) and a second repeating unit represented by any one of formulae (B-0) to (B-3). The alternating copolymer comprises alternating first and second repeating units (e.g. -(A-1)-(B-1)-(A-1)-(B-1)- . . . ), preferably regularly alternating first and second repeating units.

The alternating copolymer can, for example, be represented by the formula:

$$-[-(A-1)-(B-1)-]_n-$$

where n is an integer.

Typically, n is at least 5, preferably at least 10. For example, n may be from 5 to 500, such as from 10 to 300, more preferably from 15 to 100.

The copolymer may be a block copolymer, such as a block copolymer as represented by formula (C-1) below.

(C-1)

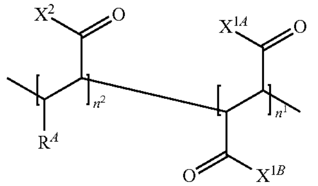

In formula (C-1), $X^{1A}$, $X^{1B}$, $R^{1A}$, $R^{1B}$, $A^{1A}$, $A^{1B}$, $Z^1$, $R^1$, $Y^1$, $L^1$, $P^1$, $Q^1$, $W^1$, $R^{1C}$ and $n^1$ are as defined above for any of formulae (A-1) to (A-3), and $R^A$, $X^2$, $R^{2A}$, $A^2$, $Z^2$, $R^2$, $Y^2$, $L^2$, $P^2$, $Q^2$, $W^2$, $R^{2C}$ and $n^2$ are as defined above for any one of formulae (B-1) to (B-3).

It is preferred that $X^{1A}$ is $A^{1A}$ and/or $X^{1B}$ is $A^{1B}$ and/or $X^2$ is $A^2$. Thus, at least one of $X^{1A}$, $X^{1B}$ and $X^2$ is $A^{1A}$, $A^{1B}$ and $A^2$ respectively. More preferably, $X^2$ is $A^2$ and at least one of $X^{1A}$ and $X^{1B}$ is $A^{1A}$ and $A^{1B}$ respectively. Even more preferably, $X^{1A}$ is $A^{1A}$, $X^{1B}$ is $A^{1B}$ and $X^2$ is $A^2$, such as represented in formula (C-2) below.

(C-2)

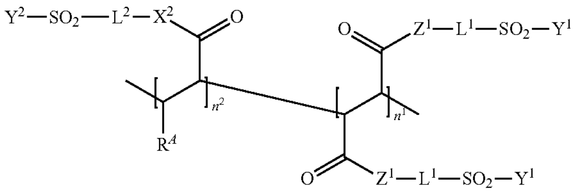

In formula (C-1) and formula (C-2) above, $R^A$ is selected from H and $C_{1-3}$ alkyl, preferably $R^A$ is selected from H and methyl. Even more preferably, $R^A$ is H.

In formula (C-1), when $X^{1A}$ is $OR^{1A}$ or $NHR^{1A}$, then it is preferred that $R^{1A}$ is $C_{1-6}$ alkyl, particularly methyl or ethyl; when $X^{1B}$ is $OR^{1B}$ or $NHR^{1B}$, then it is preferred that $R^{1B}$ is $C_{1-6}$ alkyl, particularly methyl or ethyl; and when $X^2$ is $OR^{2A}$ or $NHR^{2A}$, then it is preferred that $R^{2A}$ is $C_{1-6}$ alkyl, particularly methyl or ethyl.

In formula (C-1), $A^{1A}$ and $A^{1B}$ may be the same or different. In general, it is preferred that $A^{1A}$ and $A^{1B}$ are the same.

In formula (C-1) above, when $Z^1$ is $NR^1$, then it is preferred that $R^1$ is $C_{1-6}$ alkyl, particularly methyl or ethyl; and when $Z^2$ is $NR^2$, then it is preferred that $R^2$ is $C_{1-6}$ alkyl, particularly methyl or ethyl.

Typically, in the formulae (C-1) and (C-2) above, each $Z^1$ is preferably selected from O and NH; and $Z^2$ is preferably selected from O and NH. $Z^2$ and each $Z^1$ may be O. More preferably, $Z^2$ and each $Z^1$ is NH.

Generally, in formulae (C-1) and (C-2), each $L^1$ may be the same or different. It is preferred that each $L^1$ is the same.

Each $P^1$ may be selected from a single bond, $C_{1-10}$ alkylene and phenylene; $W^1$ may be selected from a single bond, $C_{1-10}$ alkylene and phenylene; $P^2$ may be selected from a single bond, $C_{1-10}$ alkylene and phenylene; and each $W^2$ may be selected from a single bond, $C_{1-10}$ alkylene and phenylene. More preferably, each $P^1$ may be selected from a single bond and $C_{1-10}$ alkylene; each $W^1$ may be selected from a single bond and $C_{1-10}$ alkylene; $P^2$ may be selected from a single bond and $C_{1-10}$ alkylene; and $W^2$ may be selected from a single bond and $C_{1-10}$ alkylene.

Typically, for each $L^1$ it is preferred that at least one of $P^1$, $Q^1$ and $W^1$ is not a single bond; and for $L^2$ it is preferred that at least one of $P^2$, $Q^2$ and $W^2$ is not a single bond.

When $Q^1$ is O, it is generally preferred that $P^1$ is not a single bond. When $Q^2$ is O, it is generally preferred that $P^2$ is not a single bond. More preferably, when $Q^1$ is O, it is preferred that $P^1$ is $C_{1-10}$ alkylene; and when $Q^2$ is O, it is preferred that $P^2$ is $C_{1-10}$ alkylene; more preferably $P^1$ is $C_{2-4}$ alkylene and $P^2$ is $C_{2-4}$ alkylene.

When $Q^1$ is O and $P^1$ is not a single bond, it may be preferable that $W^1$ is not a single bond. When $Q^2$ is O and $P^2$ is not a single bond, it may be preferable that $W^2$ is not a single bond. More preferably, when $Q^1$ is O, it is preferred that $P^1$ is $C_{1-10}$ alkylene and $W^1$ is $C_{1-10}$ alkylene; and when $Q^2$ is O, it is preferred that $P^2$ is $C_{1-10}$ alkylene and $W^2$ is $C_{1-10}$ alkylene; more preferably $P^1$ is $C_{2-4}$ alkylene; $W^1$ is $C_{2-4}$ alkylene; $P^2$ is $C_{2-4}$ alkylene and $W^2$ is $C_{2-4}$ alkylene.

When $Q^1$ is phenylene, it is generally preferred that $P^1$ is a single bond or $C_{1-10}$ alkylene and $W^1$ is a single bond or $C_{1-10}$ alkylene. More preferably, when $Q^1$ is phenylene, it is preferred that $P^1$ is a single bond or $C_{1-3}$ alkylene and $W^1$ is a single bond or $C_{1-3}$ alkylene.

When $Q^2$ is phenylene, it is generally preferred that $P^2$ is a single bond or $C_{1-10}$ alkylene and $W^2$ is a single bond or $C_{1-10}$ alkylene. More preferably, when $Q^2$ is phenylene, it is preferred that $P^2$ is a single bond or $C_{1-3}$ alkylene and $W^2$ is a single bond or $C_{1-3}$ alkylene.

In general, it is preferred that each $P^1$ is selected from $C_{1-10}$ alkylene, $C_{2-10}$ alkenylene and $C_{2-10}$ alkynylene; each $Q^1$ is a single bond; each $W^1$ is a single bond; $P^2$ is selected from $C_{1-10}$ alkylene, $C_{2-10}$ alkenylene and $C_{2-10}$ alkynylene; $Q^2$ is a single bond and $W^2$ is a single bond. More preferably, each $P^1$ is $C_{1-10}$ alkylene, particularly $C_{2-6}$ alkylene, such as $C_{2-5}$ alkylene; and $P^2$ is $C_{1-10}$ alkylene, particularly $C_{2-6}$ alkylene, such as $C_{2-5}$ alkylene. Even more preferably each $P^1$ is ethylene and $P^2$ is ethylene.

In formula (C-2), it is preferred that each $Y^1$ is selected from $O^-$ and OH; $Y^2$ is selected from $O^-$ and OH; $L^1$ is $C_{2-5}$ alkylene; $L^2$ is $C_{2-5}$ alkylene; $n^1$ is an integer; and $n^2$ is an integer. More preferably, $L^1$ is ethylene, $L^2$ is ethylene, $n^1$ is an integer ≥5 and $n^2$ is an integer ≥5.

Typically, in formulae (C-1) or (C-2) above, the integer represented by $n^1$ is at least 5, preferably at least 10. For example, $n^1$ may be from 5 to 500, such as from 10 to 300, more preferably from 15 to 100.

The integer represented $n^2$ is typically at least 5, preferably at least 10. For example, $n^2$ may be from 5 to 500, such as from 10 to 300, more preferably from 15 to 100.

The polymer chain may be anionic, such as when $X^{1A}$, $X^{1B}$, $X^2$, $Y^1$ or $Y^2$ is $O^-$. When the polymer chain is anionic, then $Na^+$ or $K^+$ may be present as a counter cation.

When the polymer chain is linked or coupled to a plurality of sulfonic groups, then the polymer chain (e.g. before it is linked or coupled to the plurality of sulfonic groups) has a number average (e.g. mean) molecular weight ($M_n$) of at least 300 g/mol, such as 300 to 50,000 g/mol, preferably 500 to 30,000 g/mol, more preferably 1,000 to 10,000 g/mol.

In the first aspect above, the polymer chain linked or coupled to an anti-clotting group has advantageous properties, particularly when it includes a repeating unit as represented by any one of formula (A-0) to (A-3), and especially when represented by formulae (C-1) or (C-2). The surface layer or coating may be a hydrogel. Also, the coating may be biodegradable because degradation of the polymer chain linked or coupled to an anti-clotting group may result in the formation of biocompatible by-products. In addition to reducing or preventing the clotting of blood, the anti-clotting component of the surface layer may also have excellent stability and relatively cheap, particularly when compared to other anti-clotting components in the art, such as heparin.

In a second aspect, polymerisation of a monomer comprising an anti-clotting group, such as a sulfonic group, can provide the polymer chain attached or bonded to an anti-clotting group. The monomer itself comprises, for example, a sulfonic group or a sulfonic group precursor. In this context, the polymer chain attached or bonded to an anti-clotting group or a plurality of anti-clotting groups may be referred to herein as a polymer comprising an anti-clotting group or a plurality of anti-clotting groups, particularly when the or each anti-clotting group is a sulfonic group.

The monomer comprising a sulfonic group may be a compound comprising an alkene group and a sulfonic group. Examples of such compounds include vinyl sulfonic acid, styrene sulfonic acid (e.g. 4-styrene sulfonic acid), 2-acrylamido-2-methylpropane sulfonic acid or the conjugate base thereof (e.g. the sulfonate).

The monomer comprising a sulfonic precursor group may be a compound comprising an alkene group and a sulfonic precursor group.

The polymer comprising sulfonic groups may be a homopolymer. Thus, the polymer is a homopolymer comprising sulfonic groups.

Examples of a homopolymer comprising sulfonic groups include polyvinyl sulfonic acid, polystyrene sulfonic acid, poly(2-acrylamido-2-methylpropanesulfonic acid) or a conjugate base thereof. It is preferred that the homopolymer comprising sulfonic groups is poly(2-acrylamido-2-methylpropanesulfonic acid).

The polymer comprising sulfonic groups may be a copolymer (e.g. a copolymer comprising sulfonic groups). The copolymer comprising sulfonic groups may be an alternating copolymer or a block copolymer.

The copolymer comprising sulfonic groups may be obtained from at least two monomers or from only two monomers.

The copolymer comprising sulfonic groups may be obtained from a first monomer and a second monomer, where the first monomer is different to the second monomer. The copolymer may be obtained by copolymerisation of the first monomer and the second monomer.

The first monomer comprises a sulfonic group or a sulfonic group precursor. The monomer comprising a sulfonic group may be a compound comprising an alkene group and a sulfonic group. Examples of such compounds include vinyl sulfonic acid, styrene sulfonic acid (e.g. 4-styrene sulfonic acid), 2-acrylamido-2-methylpropane sulfonic acid or the conjugate base thereof (e.g. the sulfonate). It is preferred the first monomer is 2-acrylamido-2-methylpropane sulfonic acid or the conjugate base thereof.

Similarly, the monomer comprising a sulfonic precursor group may be a compound comprising an alkene group and a sulfonic precursor group.

The second monomer comprises an alkene group. The second monomer may be selected from acrylic acid, itaconic acid, vinyl acetate and maleic acid. It is preferred that the second monomer is maleic acid.

The copolymer comprising sulfonic groups may, for example, be poly(styrenesulfonic acid-co-maleic acid) or poly(2-acrylamido-2-methylpropanesulfonic acid-co-maleic acid), preferably poly(2-acrylamido-2-methylpropanesulfonic acid-co-maleic acid).

When the polymer comprises sulfonic groups, then the polymer (e.g. including the sulfonic groups) has a number average (e.g. mean) molecular weight ($M_n$) of at least 300 g/mol, such as 300 to 50,000 g/mol, preferably 500 to 30,000 g/mol, more preferably 1,000 to 10,000 g/mol.

In general, the coating may further comprise an antimicrobial agent. The base layer and/or the surface layer may comprise the antimicrobial agent. The antimicrobial agent may, for example, be mixed with the components of the surface layer or the base layer.

The antimicrobial agent may comprise silver.

The coating of the invention is typically disposed on a surface of a medical device. The surface of the medical device may be an inner or an internal surface of the medical device (e.g. the inner surface inside a catheter) or an outer surface of the medical device. The coating may be disposed on a surface of the medical device that will come into with blood or a blood product containing platelets.

The coating may provide complete or partial coverage of the surface of the medical device.

In the coating of the invention, the surface layer is disposed on a surface of the medical device.

In some instances, the surface layer may be directly disposed on a surface of the medical device. Thus, the surface layer is in direct contact with the surface of the medical device.

The surface layer may be directly applied to a surface of the medical device, particularly if it is able to adhere or bond to this surface.

The surface of the medical device may be functionalised with a group that is able to bond to the polymer chain, such as by applying a base coating. The surface of the medical device may have amine groups. The amine groups can react with carbonyl groups in the polymer chain to form amide groups thereby bonding the surface layer of the coating to the surface of the medical device.

A plurality of layers may be disposed on a surface of the medical device. Each layer may comprise a polymer chain attached or bonded to an anti-clotting agent as defined above. The top or outermost layer will be the surface layer described above.

In general, the coating may also comprise a base layer. The base layer is typically disposed under the surface layer. There may be a layer or a plurality of layers between the base layer and the surface layer, where the or each layer comprises a polymer chain attached or bonded to an anti-clotting group, such as described above. Alternatively, the surface layer may be directly disposed on the base layer.

It is preferred that the surface layer is directly disposed on the base layer. Thus, the surface layer is typically coated onto the base layer.

The base layer may be disposed on a surface of the medical device. The base layer is typically directly disposed on a surface of the medical device. Thus, the base layer is in direct contact with the surface.

It is generally preferred that the base layer adheres or bonds, preferably adheres, to a surface of the medical device.

Typically, the base layer is biocompatible.

The base layer may comprise, or consist essentially of, a protein, preferably a human protein.

The protein may be albumin. It is preferred that the albumin is human albumin, preferably recombinant human albumin.

Albumin, particularly recombinant human albumin, can mimic the albumin found in the circulatory system of a human. It can adhere to a wide variety of surfaces, especially surfaces of medical devices, by means of a static attraction. It also provides a biopassive surface that can protect against platelet activation.

In general, the surface layer of the coating is bonded to the base layer. The surface layer may be adhesively bonded to the base layer or covalently bonded to the base layer. When the base layer comprises albumin, then the albumin may covalently bond to the polymer chain.

The invention also provides a medical device. The medical device may be used where it comes into contact with blood or a blood product containing platelets.

The coating is disposed on a surface of the medical device. Thus, the medical device has a surface coated with the coating of the invention. For convenience, the surface coated with the coating of the invention is referred to as the "coated surface". The coated surface is for use in contact with blood or a blood product containing platelets, preferably blood.

Typically, the coating has a thickness of from 0.05 μm to 300 μm, preferably 0.1 μm to 200 μm, and more preferably 1 μm to 100 μm. Generally, the thickness of the coating is selected so that it does not significantly increase the profile of the medical device for use within a patient.

The medical device may be coated with a single layer of the coating of the invention. Alternatively, the medical device may be coated with a plurality of layers of the coating of the invention. Thus, a surface of the medical device may be coated with several alternating layers of the base layer and the layer comprising the polymer chain attached to an anti-clotting group.

The medical device can be an implantable medical device or an extracorporeal medical device. The implantable medical device may be a permanently implantable medical device or a temporarily implantable medical device.

The medical device may be a transient blood contacting device, which may, for example, not be implantable or extracorporeal.

The medical device may be for in vivo use or for in vitro use. The medical device is preferably for in vivo use.

The medical device may have a component for in vivo use. It is preferred that at least a surface of the component is coated with the coating of the invention.

The coated surface of the medical device or the component of the medical device may be inserted into an area of a body, such as an afflicted area of the body. The area of the body may, for example, be an artery or a vein, such as a coronary artery or vein, a carotid artery or vein; a renal artery or vein; an iliac artery or vein; a femoral artery or vein; a popliteal artery or vein; a subclavian artery or vein; an intercranial artery or vein; the aorta; the vena cava; or a peripheral artery or vein.

Once in place, the coated surface prevents blood coagulation on and around the medical device or the component of the medical device, thereby inhibiting thrombosis, particularly sub-acute device thrombosis.

The medical device or component thereof may be a needle, catheter, a stent, a graft, a shunt, a dressing, a surgical staple, a guidewire, a cannula, a surgical instrument, an endoscope, an artificial organ or organoid (e.g. insulin secreting device), an implantable monitor or sensor, a defibrillator, a ventricular assist device, a pacemaker (e.g. cardiac pacemaker), an implantable pump (e.g. intra-aortic balloon pump or a ventricular assist pump), a cell reservoir (e.g. for stem cell placement), a prosthetic device (e.g. prosthetic heart valve), an orthopaedic device, an electrostimulation lead or lead tip, an implantable vascular access port, a blood storage bag, blood tubing, a breast implant, a pain management device, a prostate cancer treatment device, a dental implant, a focal epilepsy treatment device, a nerve regeneration conduit, a vena cava filter, a spinal repair device, a spinal cord stimulator, an internal hearing aid, a neuro aneurysm treatment device, a heart valve repair device, a intravitreal drug delivery device, a joint replacement, an ophthalmic implant, a blood oxygenator, a blood filter, a septal defect device, a hemodialysis unit, a hemoperfusion unit, a plasmapheresis unit or an anastomosis device.

Examples of catheters include a balloon or an inflation catheter, an injection catheter, a central venous catheter, an arterial catheter and an aspiration catheter. It may be preferable that the medical device is a central venous catheter or an aspiration catheter.

Examples of grafts include vascular grafts, stent grafts or bypass grafts. It may be preferable that the medical device is a bypass graft.

Examples of stents include a vascular stent, a urethra stent, a bile duct stent, a biliary stent, an oesophageal stent, and a tracheal or bronchial stent.

In general, it may be preferable that the medical device is selected from a central venous catheter, an aspiration catheter, a bypass graft, a perfusion line, a cardia bypass machine, and extracorporeal oxygenation and heat exchange circuitry.

The medical device or component thereof may comprise a metal, a polymeric material, glass or a ceramic. Thus, the coating of the invention may be coated onto a surface comprising a metal, a plastic or a ceramic.

The metal may, for example, be stainless steel, titanium, nickel, tantalum, cobalt, chromium, nickel, molybdenum, manganese, gold, platinum, iridium, silver, tungsten, a titanium alloy (e.g. nitinol), a nickel-chromium alloy (e.g. Inconel), a cobalt chromium alloy (e.g. elgiloy), a ferrous alloy, a palladium alloy, a rhenium alloy or a magnesium alloy.

The polymeric material may, for example, be cellulose acetate, cellulose nitrate, silicone, polyethylene terephthalate, polyurethane, polyamide, polyester (e.g. Nylon), polyorthoester, polyanhydride, polyether sulfone, polycarbonate, polypropylene, polyethylene or polytetrafluoroethylene.

The ceramic may, for example, include an oxide, a carbide, or a nitride of a transition metal, such as titanium oxides, hafnium oxides, iridium oxides, chromium oxides, aluminum oxides, and zirconium oxides.

The invention also provides a polymeric compound. The polymeric compound is represented by formula (C-2):

(C-2)

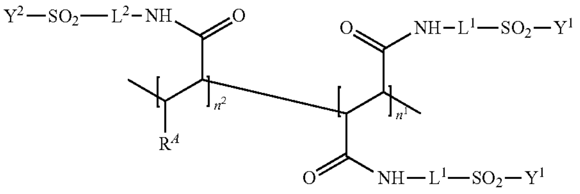

wherein:

each $Y^1$ is selected from $O^-$ and OH;

$Y^2$ is selected from $O^-$ and OH;

each $L^1$ is $C_{2-5}$ alkylene;

$L^2$ is $C_{2-5}$ alkylene;

$R^A$ is selected from H and $C_{1-6}$ alkyl, preferably selected from H and methyl;

$n^1$ is an integer; and $n^2$ is an integer.

It is preferred that each $L^1$ is ethylene and $L^2$ is ethylene.

$R^A$ is preferably selected from H and methyl. More preferably, $R^A$ is H.

The integer represented by $n^1$ is at least 5, preferably at least 10. For example, $n^1$ may be from 5 to 500, such as from 10 to 300, more preferably from 15 to 100.

The integer represented $n^2$ is typically at least 5, preferably at least 10. For example, $n^2$ may be from 5 to 500, such as from 10 to 300, more preferably from 15 to 100.

Also provided by the invention are uses of the coating and the medical device.

The coating or a medical device comprising the coating can be used in the treatment of the human or animal body by surgery or therapy and/or in a diagnostic method practised on the human or animal body.

The diagnostic method practised on the human or animal body is typically an in vivo diagnostic method.

The diagnostic method or the treatment by surgery or therapy typically involves the coating, or the medical device comprising the coating, coming into contact with blood.

The coating or a medical device comprising the coating is for use in reducing or preventing the clotting of blood, preferably reducing or preventing the clotting of blood on the coated surface of the medical device.

The invention also provides a method of reducing or preventing the clotting of blood. The method comprises contacting a medical device of the invention with blood. The medical device is used in its normal manner, except that the presence of coating inhibits or prevents the formation of blood clots, particularly on the coated surface of the medical device.

One aspect of the method is an in vitro method. For example, the method may be an in vitro method of reducing or preventing the clotting of blood when processing the blood. The blood may be processed to produce processed blood or a blood product, such as a blood product for storage.

The method may comprise contacting the medical device with blood, wherein the blood has been removed from a human or animal body. The blood may be contacted with the medical device to process the blood.

The method may not include a step of administering the processed blood or the blood product to the human or animal body. The blood product or processed blood may not be returned to the human or animal body, preferably the human or animal body from which the blood was removed.

A further aspect of the method is a diagnostic method, particularly an in vitro and/or ex vivo diagnostic method.

The method may relate to a method of reducing or preventing the clotting of blood in a diagnostic procedure. The method may comprise contacting the medical device with blood to obtain diagnostic information. The medical device may be contacted with pre-obtained or pre-delivered blood.

The diagnostic procedure is not carried out on the human or animal body or the diagnostic procedure is carried out on a non-living (e.g. dead) human or animal body. Thus, the diagnostic method may not include a step of removing blood from a human or animal body, particularly a living human or animal body.

The invention also provides a method of manufacturing a coating for a medical device, particularly a coating comprising a surface layer, which comprises a polymer chain attached or bonded to an anti-clotting group according to the first aspect.

The method comprises attaching or bonding (e.g. by a coupling reaction) a compound comprising an anti-clotting agent to a polymer using a coupling agent. The compound comprising an anti-clotting agent may be attached or bonded to the polymer by forming an amide group.

The invention further provides a kit for coating a medical device, particularly when the coating has a surface layer, which comprises a polymer chain attached or bonded to an anti-clotting group according to the first aspect.

The kit comprises: (a) a polymer, (b) compound comprising an anti-clotting group, (c) a coupling agent, and optionally (d) a coating for forming the base layer.

The polymer may, for example, be a dispersed in a solution or a gel.

In the method of manufacture or the kit, the polymer forms the polymer chain, which is attached or bonded to an anti-clotting group.

Typically, the polymer includes a repeating unit represented by formula (D-1) below.

(D-1)

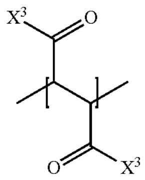

In formula (D-1) above, $X^3$ is selected from OH, $OR^{3A}$, $NH_2$ and $NHR^{3A}$; and $R^{3A}$ is selected from $C_{1-6}$ alkyl, $C_{6-10}$ aryl and $C_{6-10}$ aryl-$C_{1-6}$ alkyl.

It is preferred that $X^3$ is selected from OH and $NH_2$, more preferably $X^3$ is OH.

The repeating unit represented by formula (D-1) above may, for example, be obtainable from a maleic acid monomer or a maleimide monomer.

The polymer may include a repeating unit represented by formula (D-2) below.

(D-2)

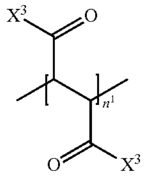

In formula (D-2), $X^3$ is as defined above and $n^1$ is an integer. Typically, $n^1$ is at least 5, preferably at least 10. For example, $n^1$ may be from 5 to 500, such as from 10 to 300, more preferably from 15 to 100.

The polymer may be a copolymer. The copolymer is typically a block copolymer, such as a block copolymer as represented by formula (D-3) below.

(D-3)

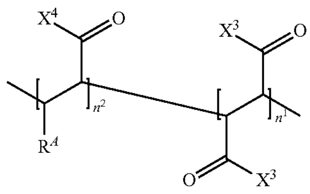

In formula (D-3), $X^3$ and $n^1$ are as defined above for formulae (D-1) or (D-2); $R^A$ is selected from H and $C_{1-6}$ alkyl; $X^4$ is selected from OH, $OR^4$, $NH_2$ and $NHR^4$; $R^4$ is selected from $C_{1-6}$ alkyl, $C_{6-10}$ aryl and $C_{6-10}$ aryl-$C_{1-6}$ alkyl; and $n^2$ is an integer.

$R^A$ is preferably selected from H and $C_{1-3}$ alkyl. More preferably $R^A$ is selected from H and methyl. Even more preferably, $R^A$ is H.

It is preferred that $X^4$ is selected from OH and $NH_2$, more preferably $X^4$ is OH.

Typically, the integer represented by $n^2$ is at least 5, preferably at least 10. For example, $n^2$ may be from 5 to 500, such as from 10 to 300, more preferably from 15 to 100.

The compound comprising an anti-clotting group may be represented by formula (E-1):

$$Z^3\text{-}L^3\text{-}SO_3H \quad (E\text{-}1)$$

wherein:

$Z^3$ is selected from OH, $NH_2$ and $NHR^3$;

$R^3$ is selected from $C_{1-6}$ alkyl, $C_{6-10}$ aryl and $C_{6-10}$ aryl-$C_{1-6}$ alkyl;

$L^3$ is represented by formula (L-3):

$$—P^3\text{-}Q^3\text{-}W^3— \quad (L\text{-}3)$$

wherein:

$P^3$ is selected from a single bond, $C_{1-10}$ alkylene, $C_{2-10}$ alkenylene, $C_{2-10}$ alkynylene and phenylene;

$Q^3$ is selected from a single bond, O, NH, $NR^{3C}$ and phenylene;

$W^3$ is selected from a single bond, $C_{1-10}$ alkylene, $C_{2-10}$ alkenylene, $C_{2-10}$ alkynylene and phenylene; and $R^{3C}$ is selected from $C_{1-6}$ alkyl, $C_{6-10}$ aryl and $C_{6-10}$ aryl-$C_{1-6}$ alkyl.

It is preferred that $Z^3$ is $NH_2$.

$P^3$ is typically selected from a single bond, $C_{1-10}$ alkylene and phenylene; and $W^3$ may be selected from a single bond, $C_{1-10}$ alkylene and phenylene. More preferably, $P^3$ may be selected from a single bond and $C_{1-10}$ alkylene; and $W^3$ may be selected from a single bond and $C_{1-10}$ alkylene.

Alternatively, $P^3$ is selected from $C_{1-10}$ alkylene, $C_{2-10}$ alkenylene and $C_{2-10}$ alkynylene; $Q^3$ is selected from O, NH and $NR^{3C}$ and $W^3$ is a single bond. More preferably $Q^3$ is selected from O and NH.

Typically, for $L^3$ it is preferred that at least one of $P^3$, $Q^3$ and $W^3$ is not a single bond.

When $Q^3$ is O, it is generally preferred that $P^3$ is not a single bond. More preferably, when $Q^3$ is O, it is preferred that $P^3$ is $C_{1-10}$ alkylene, more preferably $P^3$ is $C_{2-4}$ alkylene.

When $Q^3$ is O and $P^3$ is not a single bond, it may be preferable that $W^3$ is not a single bond. More preferably, when $Q^3$ is O, it is preferred that $P^3$ is $C_{1-10}$ alkylene and $W^3$ is $C_{1-10}$ alkylene, more preferably $P^3$ is $C_{2-4}$ alkylene and $W^3$ is $C_{2-4}$ alkylene.

When $Q^3$ is phenylene, it is generally preferred that $P^3$ is a single bond or $C_{1-10}$ alkylene and $W^3$ is a single bond or $C_{1-10}$ alkylene. More preferably, when $Q^3$ is phenylene, it is preferred that $P^3$ is a single bond or $C_{1-3}$ alkylene and $W^3$ is a single bond or $C_{1-3}$ alkylene.

In general, it is preferred that $P^3$ is selected from $C_{1-10}$ alkylene, $C_{2-10}$ alkenylene and $C_{2-10}$ alkynylene; $Q^3$ is a single bond and $W^3$ is a single bond. More preferably, $P^3$ is $C_{1-10}$ alkylene, particularly $C_{2-6}$ alkylene, such as $C_{2-5}$ alkylene. Even more preferably $P^3$ is butylene, propylene or ethylene, preferably ethylene.

The compound represented by formula (E-1) may be taurine.

The coupling agent may be a carbodiimide coupling agent. Examples of carbodiimide coupling agents include N,N'-dicyclohexylcarbodiimide (DCC), N,N'-diisopropylcarbodiimide (DIC) and 1-ethyl-3-(3-dimethylaminopropyl) carbodiimide (EDC). It is preferred that the coupling agent is EDC.

In the kit of the invention, the coupling agent may be a powder.

The coating for forming the base layer may be a solution, a suspension or a gel comprising a protein, preferably a human protein. It is preferred that the coating for forming the base layer is a solution, such as a stabilised solution. As mentioned above, the protein may be albumin. It is preferred that the albumin is human albumin, preferably recombinant human albumin.

The method of manufacture of the invention involves coupling a carboxylic acid or an amide group of the polymer to a hydroxy group or an amino group of the compound comprising an anti-clotting agent using the coupling agent. Such coupling reactions are known in the art.

The coupling reaction produces a polymer chain attached or bonded to an anti-clotting group. Any remaining coupling agent can be removed to form a coating, such as by rinsing with water.

The coating can be applied to a surface of the medical device by, for example, dip-coating, spray, wash, brush, roller, or spin coating. Alternatively, the coating may be pumped through the medical device, such as to coat an inner surface of the medical device.

The thickness of the coating may be controlled by altering soaking time, flow rate etc and the number of coating steps. Each coating can be provided on a surface of the medical device as described herein in a series of applications. The number of applications may be selected to provide individual coated layers of suitable thickness, as well as a desired total number of multiple coatings, as desired.

When the coating comprises a base layer, then the base layer may be applied to a surface of the medical device before the surface layer. The surface of the medical device may be coated with a solution, a suspension or a gel comprising a protein, preferably a human protein. The protein may be albumin. It is preferred that the albumin is human albumin, preferably recombinant human albumin.

The invention may also provide a method of coating a surface of a medical device. The method comprises applying a coating, such as described above, to a surface of the medical device. The coating is applied to form a surface layer and may, for example, be applied as described above.

The coating for the surface layer may be pre-formed. Thus, the polymer chain attached or bonded to an anti-clotting group in accordance with the invention may be directly applied to a surface of the medical device or, when present, to a base layer on a surface of the medical device.

Alternatively, the polymer chain attached or bonded to an anti-clotting group may be formed (e.g. in situ) on a surface of the medical device or, when present, a base layer on a surface of the medical device. Thus, the coating can be manufactured on a surface of the medical device or the base layer, preferably in accordance with the method of manufacturing a coating for a medical device. Thus, a compound comprising an anti-clotting agent, a polymer and a coupling agent may be applied to a surface of the medical device or, when present, the base layer. The compound comprising an anti-clotting agent may be attached or bonded to the polymer using the coupling agent (e.g. to form the coating), as described for the method of manufacturing a coating for a medical device.

The method may comprise attaching or bonding a compound comprising an anti-clotting agent to a polymer using a coupling agent. The anti-clotting agent may also be referred to as a hemocompatibility agent (i.e. the term "anti-clotting agent" is synonymous with the term "hemocompatibility agent").

The surface of the medical device may have already been coated with a base layer. Thus, the method may also comprise applying a base layer to a surface of the medical device or applying a coating to a medical device to form a base layer, such as described above. The coating, in this context, is the coating for forming a base layer.

When a base layer has already been applied to a surface of the medical device, then the coating applied to form a surface layer may be applied to the base layer on a surface of the medical device.

EXAMPLES

The invention will now be illustrated by the following non-limiting examples.

Example 1

Bovine Serum Albumin Coating

A bovine serum albumin solution was prepared in a distilled water buffer at a pH of 4.5 (via HCl & NaOH titration) and a concentration of approximately 25 mg/100 mL.

Samples of PVC tubing were incubated at room temperature in this solution for 0-1 hr with gentle swirling to produce samples coated with bovine serum albumin.

All of the albumin coated samples were subsequently soaked for 15 minutes with DI water and dried.

Poly(Maleic Acid-Co-Acrylic Acid) Coating

A 1 mL/200 mL solution of poly(maleic acid-co-acrylic acid) polymer at pH 4.5 was prepared. Samples were incubated at room temperature in this solution for 0-1 hr with gentle swirling. All samples were subsequently soaked for 15 minutes with de-ionised (DI) water and dried.

To crosslink the albumin and the poly(maleic-co-acrylic acid), 500 mg of EDC (1-ethyl-3-(3-dimethylaminopropyl) carbodiimide hydrochloride) in distilled water at pH 4.5 was used. The samples coated with both albumin and the poly (maleic-co-acrylic acid) were incubated in this solution for 15 mins to 1 hr. The coated samples were then removed and rinsed with DI water and dried.

Sulfonic Acid Group Modified Coating

The samples were then treated to cross-link the poly (maleic-co-acrylic acid) polymer with taurine. A distilled water solution at pH 8.3 was prepared via titration of HCl and NaOH. 500 mg of EDC (1-ethyl-3-(3-dimethylamino-propyl)carbodiimide hydrochloride) and 500 mg of taurine (2-amino sulfonic acid) were added to the coated samples in 100 mL of the pH 8.3 solution. The coated samples were incubated from 3-24 hrs to allow the crosslinking to happen. The coated samples were then rinsed with DI water and dried.

The coated samples were treated with toluidine blue. Toluidine blue has a high affinity for acidic groups, such as any sulfonic acid groups present in the coating. After the treatment, the coated samples showed a blue/purple colour, which confirmed the presence of the sulfonic acid groups.

Heparin Coating (Comparative)

A commercially available coating was obtained from Coatings2Go™ and applied to a substrate using the instructions that were provided. The coating was a hydrophilic coating and contained polymeric repeating units derived from an acrylate. Heparin was bound to the coated substrate by chemical crosslinking using EDC as described above.

Studies and Results

Whole Blood Assay Method

Whole blood assay experiments were performed to measure the anti-coagulation activity of the coating.

Experiment 1—Ovine Whole Blood

Experiments were carried out using citrated ovine whole blood within 24 hours after phlebotomy. Blood was recalcified using calcium chloride 0.025 M (Hemosil) at a ratio of 9:1 immediately before the start of the experiment (T0). The experiments were performed with the following PVC tube samples.

TABLE 1

| Sample Types | |
|---|---|
| Sample | Coating on PVC tubing |
| A | Heparin |
| B | Bovine albumin |
| C | No coating |
| D | Sulfonic acid group modified poly(maleic acid-co-acrylic acid) coating |

Triplicates of each sample were incubated with 1 mL of blood at 37° C. in static conditions (T3 hr, T6 hr and T12 hr) prior to taking measurements. As shown in Table 1, an un-coated 2 mL tube (sample C) was used as a control. Tubes were weighed before and after incubation. Subsequently, tubes were inverted on a weighing boat and excess liquid absorbed using tissue paper without touching the clot. The weight of each clot was measured using a fine balance and was obtained by subtracting the weight of the weighing boat. The results are shown in Table 2 and in the histogram of FIG. 1.

TABLE 2

| Clot Weights (g) | | | | | |
|---|---|---|---|---|---|
| Sample | triplicate 1 | triplicate 2 | triplicate 3 | mean | sd |
| A | 0.367 | 0.432 | 0.363 | 0.387 | 0.039 |
| B | 0.380 | 0.410 | 0.413 | 0.401 | 0.018 |
| C | 0.646 | 0.625 | 0.608 | 0.626 | 0.019 |
| D | 0.359 | 0.354 | 0.368 | 0.360 | 0.007 |
| Control (no PVC tube) | 0.690 | | | 0.690 | |

Figure 2:
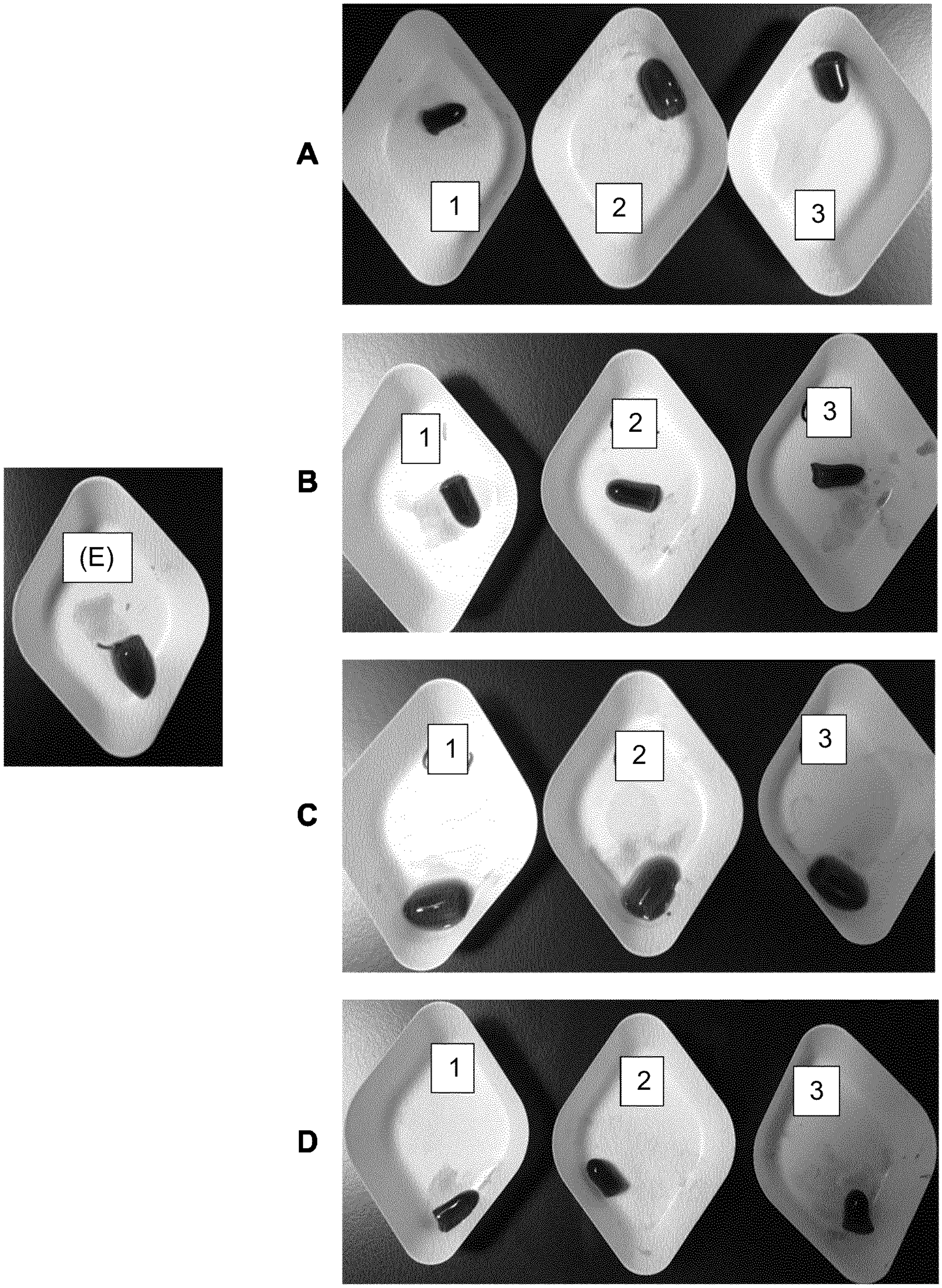
FIG. 2 is a series of photographs showing the clots on samples from a whole blood assay experiment after a 12 h incubation time.

Each clot was also photographed (see FIG. 2). The photograph on the left (labelled (E)) corresponds to a control. The photographs on the right (labelled (A) to (D) to correspond with the samples in Table 2 above) show the triplicates for each type of sample. The differences between the clot formations for the uncoated samples (C) and the other samples ((A), (B) and (D)) can be seen in the photographs.

No coagulation was observed in the control tube (E) or any of the four samples (A) to (D) after 3 h. Very limited coagulation was observed after 6 h, but no real solid clot formed. After 12 h, coagulation was clearly observed for samples (A), (B) and (D). Measurements were carried out (see Table 2, and FIG. 1) of the clots. The statistical analyses below were then performed followed by Post-Hoc tests.

Statistical Analysis

One-way ANOVA was carried out on all four samples followed by Tukey HSD Test.

TABLE 3

| Descriptive Statistics | | | | | |
|---|---|---|---|---|---|
| Treatment | A | B | C | D | Pooled Total |
| Observations N | 3 | 3 | 3 | 3 | 12 |
| Sum | 1.162 | 1.203 | 1.879 | 1.081 | 5.325 |
| Mean | 0.3873 | 0.401 | 0.6263 | 0.3603 | 0.4438 |
| Sum of squares | 0.4531 | 0.4831 | 1.1776 | 0.3896 | 2.5034 |
| Sample variance | 0.0015 | 0.0003 | 0.0004 | 0.0001 | 0.0128 |
| Sample std. dev. | 0.0387 | 0.0182 | 0.019 | 0.0071 | 0.113 |
| Std. dev. of mean | 0.0224 | 0.0105 | 0.011 | 0.0041 | 0.0326 |

TABLE 4

| One-way ANOVA | | | | | |
|---|---|---|---|---|---|
| Source | Sum of squares | Degrees of freedom | Mean square | F statistic | p-value |
| Treatment | 0.1359 | 3 | 0.0453 | 80.6864 | 2.54E−06 |
| Error | 0.0045 | 8 | 0.0006 | | |
| Total | 0.1404 | 11 | | | |

In conclusion from the ANOVA analysis, the p-value in Table 4 corresponding to the F-statistic of one-way ANOVA is lower than 0.05, suggesting that the one or more treatments are significantly different.

The post-hoc tests would likely identify which of the pairs of treatments are significantly different from each other (Tukey HSD test).

TABLE 5

| Tukey HSD Test | | | |
|---|---|---|---|
| Treatments pair | Q statistic | p-value | Inference |
| A vs C | 17.470 | 0.001 | ** p < 0.01 |
| A vs D | 1.974 | 0.534 | Insignificant |
| B vs C | 16.471 | 0.001 | ** p < 0.01 |
| C vs D | 19.443 | 0.001 | ** p < 0.01 |

In the Tukey HSD Test, when the p-value corresponding to the F-statistic of one-way ANOVA is lower than 0.01, the result strongly suggests that the effect associated with the pair of samples was significantly different.

There was no statistically significant difference in clot formation between the coating of the invention (D) and Heparin coating (A).

Experiment 2—Ovine Whole Blood

The experimental conditions described above for the whole blood assay in Experiment 1 were also used for this experiment. Briefly, samples were incubated in triplicates overnight with 1 mL of blood at 37° C. in static conditions. Citrated whole blood was recalcified using calcium chloride 0.025 M (Hemosil) at a ratio of 9:1 immediately before the start of the experiment (T0). The samples shown in Table 6 were prepared using the methods described above.

TABLE 6

| Sample Types | |
|---|---|
| Sample | Coating on PVC tubing |
| B3 | No coating |
| B4 | Sulfonic acid group modified poly(maleic acid-co-acrylic acid) coating |
| B5 | Heparin coating |

A triplicate control consisting of liquid heparin at a final concentration of 0.5 U/mL was included in the experiment (labelled "H").

Figure 3:
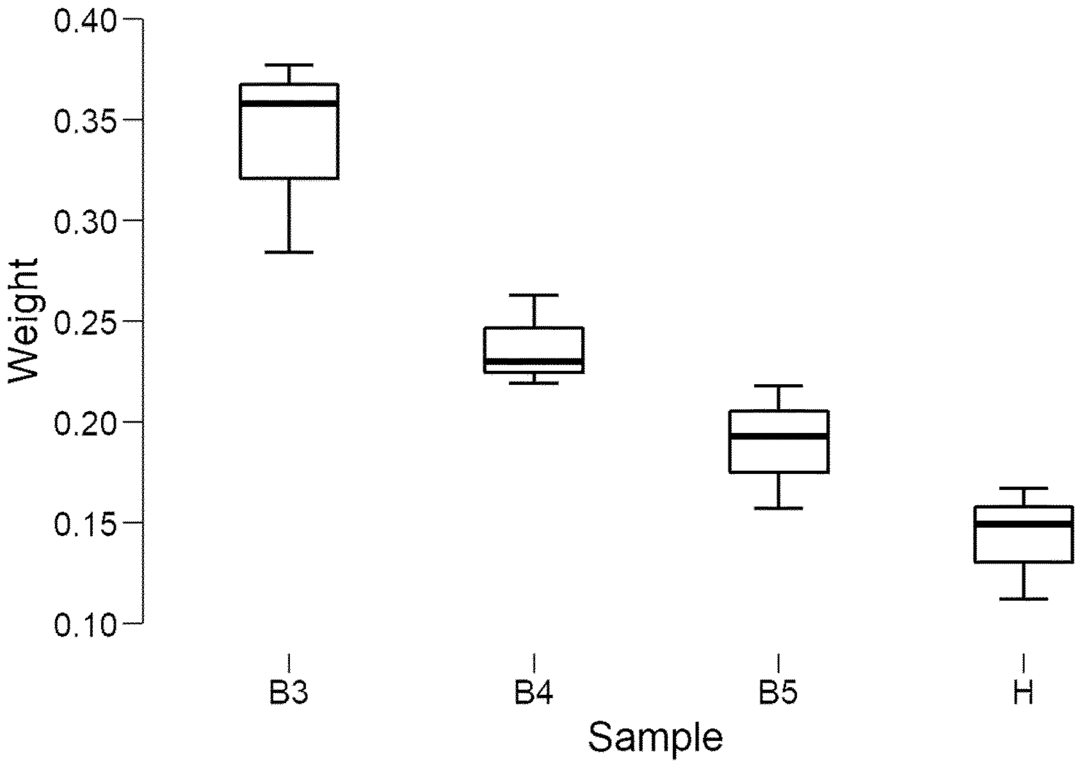
FIG. 3 is a boxplot showing the clot weights (g) from samples obtained from a second whole blood assay experiment.
Figure 4:
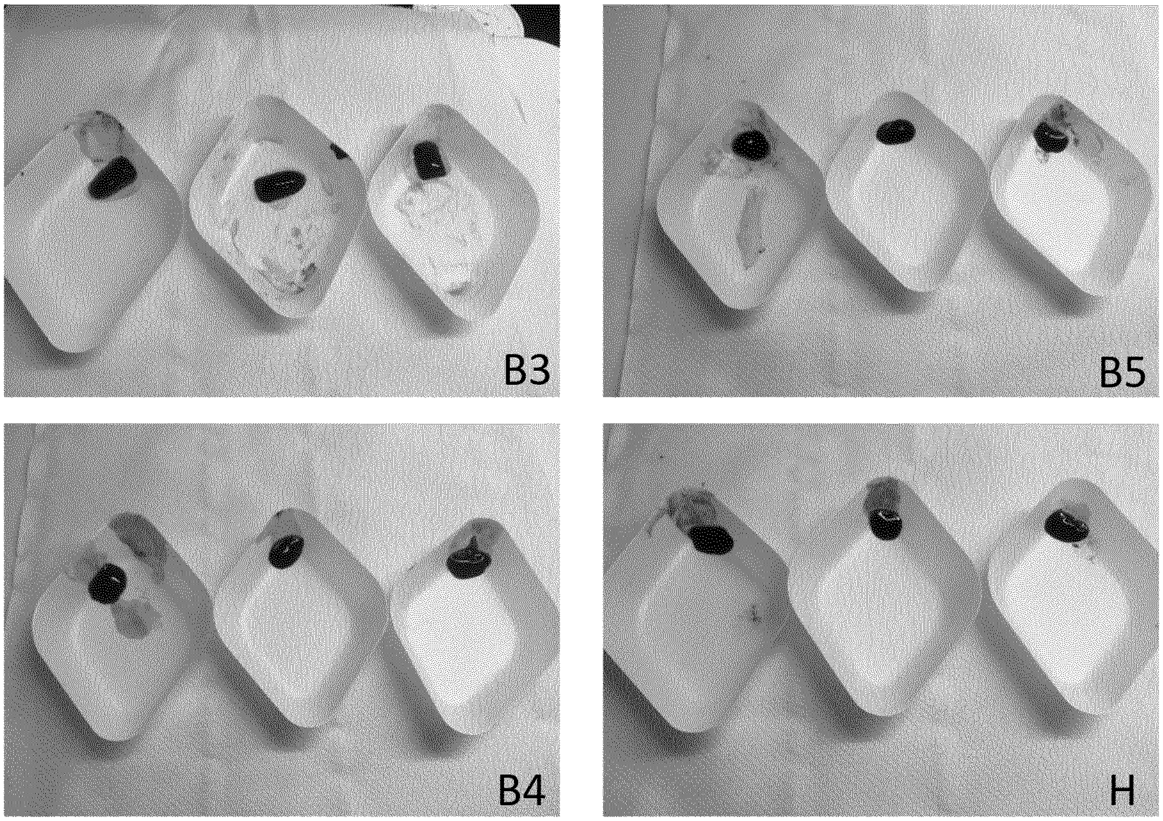
FIG. 4 is a series of photographs showing the clots on samples from a second whole blood assay experiment.

Clots were weighed on a fine balance (see Table 7 and FIG. 3) as described previously and were also photographed (see FIG. 4).

TABLE 7

| Clot Weights (g) | | | | |
|---|---|---|---|---|
| | Weight (g) | | | |
| | B3 | B4 | B5 | H |
| Valid | 3 | 3 | 3 | 3 |
| Mean | 0.3397 | 0.2373 | 0.1893 | 0.1427 |
| Std. Deviation | 0.04914 | 0.02290 | 0.03066 | 0.02804 |
| Minimum | 0.2840 | 0.2190 | 0.1570 | 0.1120 |
| Maximum | 0.3770 | 0.2630 | 0.2180 | 0.1670 |

Statistical analysis in the form of analysis of variance between the four sample types were performed followed by Post-Hoc tests. The Levene test assumed equality of variance (p=391) hence ANOVA was carried out (see Table 8) followed by Tukey and Bonderroni tests (Table 3).

TABLE 8

| One-way ANOVA | | | | | |
|---|---|---|---|---|---|
| Cases | Sum of squares | Degrees of freedom | Mean square | F statistic | p-value |
| Treatment | 0.064 | 3 | 0.021 | 18.29 | <0.001 |
| Error | 0.009 | 8 | 0.001 | | |

The p-value in Table 8 corresponding to the F-statistic of one-way ANOVA suggests samples display significant differences. The PostHoc tests below display a pairwise statistical comparison between samples.

TABLE 9

| Post Hoc Tests | | | | | |
|---|---|---|---|---|---|
| Treatments pair | Mean Difference | SE | t | $p_{tukey}$[1] | $p_{bonf}$[2] |
| B3 vs B4 | 0.102 | 0.028 | 3.670 | 0.026 | 0.038 |
| B3 vs B5 | 0.150 | 0.028 | 5.391 | 0.003 | 0.004 |
| B3 vs H | 0.197 | 0.028 | 7.065 | <0.001 | <0.001 |
| B4 vs B5 | 0.048 | 0.028 | 1.721 | 0.374 | 0.741 |
| B4 vs H | 0.095 | 0.028 | 3.395 | 0.038 | 0.057 |
| B5 vs H | 0.047 | 0.028 | 1.674 | 0.395 | 0.797 |

[1]$p_{tukey}$ corresponds to the p-value for the Tukey HSD test;
[2]$p_{bonf}$ corresponds to the p-value for the Bonferroni test.

Both Post Hoc tests showed similar results (see Table 9, particularly with $p_{tukey}$ and $p_{bonf}$). Sample B3 shows significant differences with all other samples, i.e. B4, B5 and control H. Sample B4 is significantly different to control H but not to sample B5. Sample B5 and control H do not display significant differences.

Experiment 3—Human Whole Blood

The experimental conditions for the whole blood assays described above were also used for this experiment, except that human blood was used, there were additional replicates (six instead of three), a saline rinse of the tubes before experimentation (PBS 0.1M) and a spinning step of the clots prior to measurements (0.1 g, 1 min).

Figure 5:
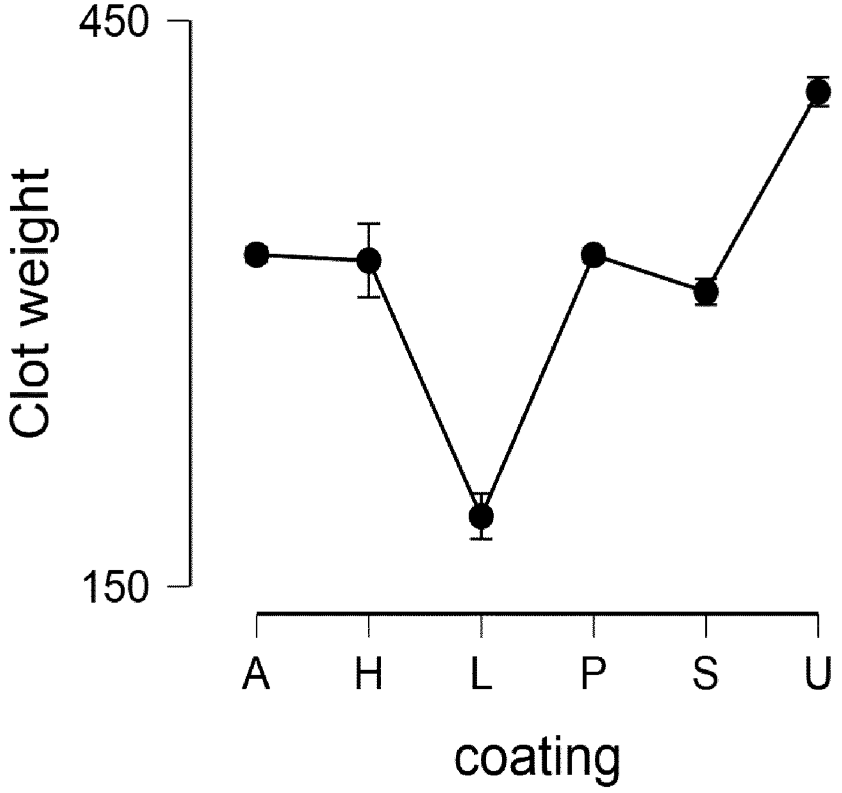
FIG. 5 is a graph showing the mean clot weights from samples obtained from a human whole blood assay experiment.
Figure 6:
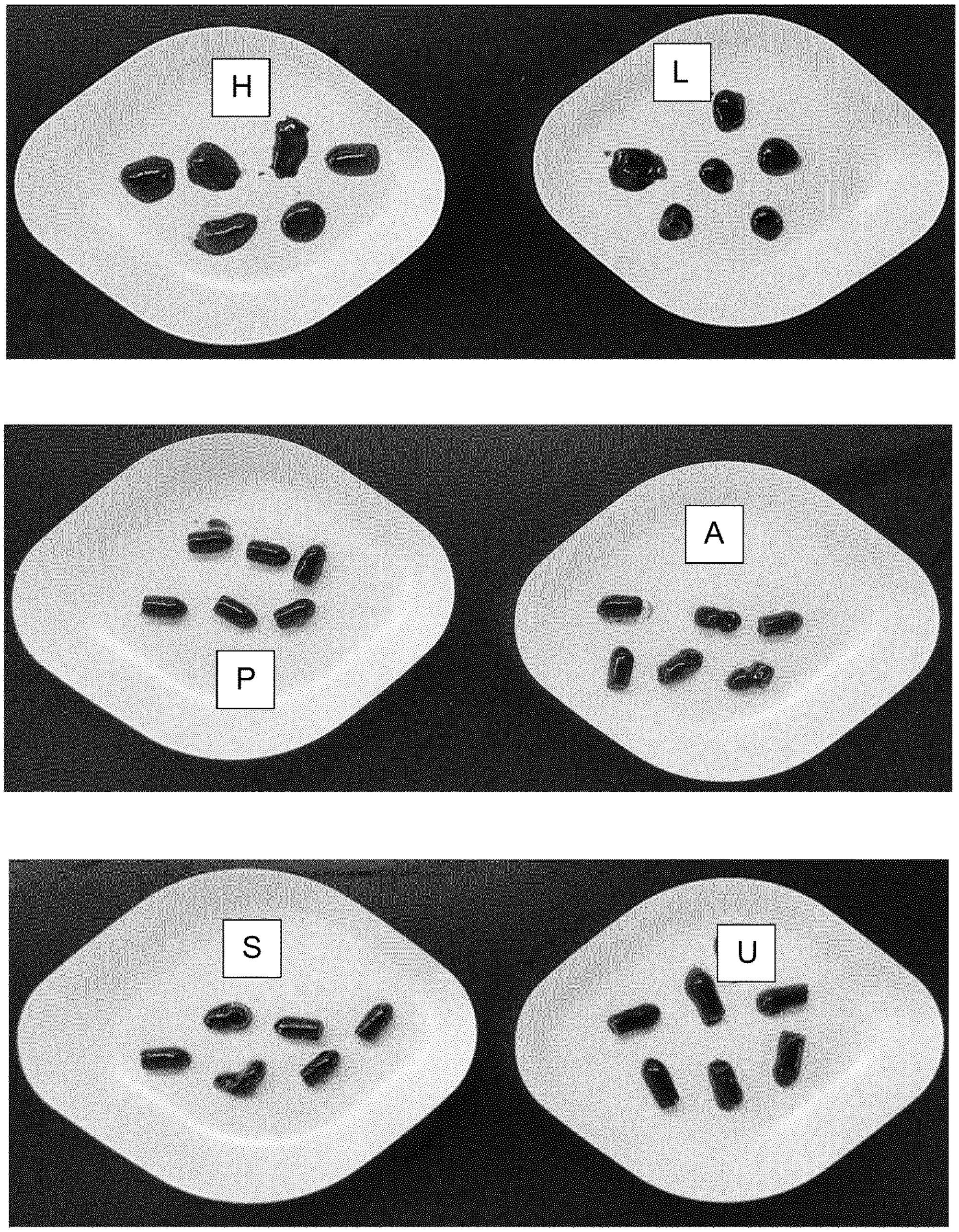
FIG. 6 is a series of photographs showing the clots on samples from a human whole blood assay experiment after incubation overnight.

Human whole blood was collected by phlebotomy in sodium citrated buffer (3.2%) the previous day (4 pm) and stored at 4° C. overnight prior to experimentation. Blood was re-calcified using calcium chloride (2.06%) at a ratio of 9:1 immediately before the start of the experiment. Samples (six replicates of each) were incubated overnight with 1 mL of blood at 37° C. in static conditions. 2 mL polypropylene eppendorf tubes were coated as described above. The samples tested were a heparin coated tube (H), an albumin coated tube (A), a sulfonic acid group modified coating of the invention (S), a tube coated with PEG (P) and uncoated tube (U). An additional control (L) consisting of liquid heparin at a final concentration of 0.5 U/mL was included in the experiment. Clots were weighed on a fine balance. The results are shown in Table 10 and are represented graphically in FIG. 5. Photographs of the samples are shown in FIG. 6. The masses from clots of whole blood after an overnight incubation in tubes coated with various compounds were compared (weights and photographs).

TABLE 10

| Clot Weights (mg) | | | |
|---|---|---|---|
| Coating | Mean | SD | N |
| A | 325.833 | 9.261 | 6 |
| H | 322.667 | 47.869 | 6 |
| L | 187.167 | 29.539 | 6 |
| P | 325.667 | 9.004 | 6 |
| S | 306.167 | 16.833 | 6 |
| U | 412 | 18.755 | 6 |

Statistical analysis in the form of analysis of variance between the six sample types (Table 11) were performed followed by Post-Hoc tests (Table 4).

TABLE 11

| ANOVA-Clot Weight | | | | | | |
|---|---|---|---|---|---|---|
| Cases | Homogeneity Correction | Sum of Squares | df | Mean Square | F | P |
| Coating | None | 156797.222 | 5.000 | 31359.444 | 47.442 | <0.001 |
| Coating | Brown-Forsythe | 156797.222 | 5.000 | 31359.444 | 47.442 | <0.001 |
| Coating | Welch | 156797.222 | 5.000 | 31359.444 | 44.710 | <0.001 |
| Residual | None | 19830.000 | 30.000 | 661.000 | | |
| Residual | Brown-Forsythe | 19830.000 | 12.623 | 1570.892 | | |
| Residual | Welch | 19830.000 | 13.554 | 1463.060 | | |

Note.
Type III Sum of Squares

TABLE 12

| Post Hoc Test Result | | | | | | |
|---|---|---|---|---|---|---|
| Treatments pair | | Mean Difference | SE | t | $p_{tukey}$ | $p_{bonf}$ |
| A vs | H | 3.167 | 14.844 | 0.213 | 1.000 | 1.000 |
| | L | 138.667 | 14.844 | 9.342 | <0.001 | <0.001 |
| | P | 0.167 | 14.844 | 0.011 | 1.000 | 1.000 |
| | S | 19.667 | 14.844 | 1.325 | 0.769 | 1.000 |
| | U | −86.333 | 14.844 | −5.816 | <0.001 | <0.001 |
| H vs | L | 135.500 | 14.844 | 9.128 | <0.001 | <0.001 |
| | P | −3.000 | 14.844 | −0.202 | 1.000 | 1.000 |
| | S | 16.500 | 14.844 | 1.112 | 0.873 | 1.000 |
| | U | −89.500 | 14.844 | −6.030 | <0.001 | <0.001 |

TABLE 12-continued

| Post Hoc Test Result | | | | | | |
|---|---|---|---|---|---|---|
| Treatments pair | | Mean Difference | SE | t | $p_{tukey}$ | $p_{bonf}$ |
| L vs | P | −138.500 | 14.844 | −9.331 | <0.001 | <0.001 |
| | S | −119.000 | 14.844 | −8.017 | <0.001 | <0.001 |
| | U | −225.000 | 14.844 | −15.158 | <0.001 | <0.001 |
| P vs | S | 19.500 | 14.844 | 1.314 | 0.775 | 1.000 |
| | U | −86.500 | 14.844 | −5.827 | <0.001 | <0.001 |
| S vs | U | −106.000 | 14.844 | −7.141 | <0.001 | <0.001 |

For the coatings, clot S was the lightest and clot U presented the highest mass. Sample L from incubation of whole blood with liquid heparin was the lightest as expected. Visually, clot samples L and H, both in contact with heparin, looked more liquid as opposed to all other clots, resembling those obtained in uncoated tubes (negative control).

Statistical analysis in the form of an analysis of variance (ANOVA) showed significant differences between the six types of samples. Tukey Post Hoc test pinpointed the differences between samples L and all others as expected. Differences were also significant between samples U and S but not between S and H.

Example 2

The coatings of the invention were compared with commercially available coatings using an in vitro Chandler Loop System™.

Coatings

The coatings that were tested are shown in Table 13 below. Each coating was tested by applying the coating to a tube. The commercially available reference coatings are numbered R1 to R4. Coating number 5 is the coating of the invention (the sulfonic acid group modified coating) and was prepared as described in Example 1. The length of each coated sample was 47 cm and "n" is the number of blood donors.

TABLE 13

| Coatings Tested | |
|---|---|
| Coating No. | Name |
| R1 | Bioline ™ (⅜", 47 cm; n = 5) |
| R2 | Dideco ™ (⅜", 47 cm; n = 5) |
| R3 | Medtronic Intercept ™ (⅜", 47 cm; n = 3) |
| R4 | Medtronic Balance ™ biosurface (⅜", 47 cm; n = 5) |
| 5 | Smart reactors-SR 004 (⅜", 47 cm; n = 5) |

As controls, both a blood sample control was used to provide a baseline and an uncoated tube was used as a reference.

Chandler-Loop Model

Before a coating can be used in a clinical setting, it is imperative to test the hemocompatibility of blood contacting medical devices under standardized conditions. The in-vitro Chandler-Loop model is a closed system in which the effect of artificial surfaces to initiate the different cascade reactions of the human hemostatic system (coagulation, cell alteration, complement and inflammation) can be investigated. In the Chandler Loop System, polymer tubes, partly filled with blood, are formed into re-closable loops and are rotated with a rotation speed between 10-40 RPM in a temperature controlled water basin, to simulate arterial flow conditions. A multiparametric approach was used to assess the surfaces, which was not only restricted to the thrombosis evaluation, but also measured expressive markers having central importance within the hemostatic system. Coating tubing were tested for their hemocompatibility by using an in-vitro Chandler-Loop model with fresh human whole blood.

The control (baseline) had no blood-loop contact, whereas each coated tube was subjected to 60 minutes of blood perfusion in the loop. Blood was used from 5 healthy volunteers. The quality of the blood used for these experiments is of decisive importance. The following exclusion criteria for the blood donators have to be strictly fulfilled: hemostasis-affecting drug-taking in the last 2 weeks.

TABLE 14

| Parameters for Chandler Loop model | |
|---|---|
| Blood Drawing | Without stasis, carefully by venipuncture with "butterflies" (ø 1.4 mm) directly and sterile in pre-anticoagulated containers (Sarstedt, Nümbrecht, Germany). |
| Anticoagulation | 1 IU/ml Heparin (Heparin-Natrium LEO 25000 I.E./5 ml (LEO Pharma GmbH, Neu-Isenburg, Germany). |
| Blood volume | 20 ml for each loop. |
| Speed | 30 rpm. |
| Temperature | Normothermia 37° C., controlled by a hypothermic regulator (type Q 102, Haake, Berlin, Germany). |
| Blood sampling | From each sample following blood volumes were taken: (a) 2.7 ml EDTA blood for blood cells and SC5b-9; (b) 3.0 ml citrated blood for TAT and hemolysis; (c) 2.7 ml blood in CTAD medium for β-TG. |
| Sample storage | The samples were centrifuged immediately with corresponding programs with a cryofuge (Hettich Rotana 460R). The plasmas are then aliquoted in 100-200 μl samples, shock-frozen in liquid nitrogen and stored at −20° C. for subsequent chemical analyses. |

Thrombogenicity

The SEM (LEO 1430, Zeiss) analyses of 2 experiments (donor 1 and 2) showed no signs of real thrombus formation in all groups. Low platelet sticking was observed at the surface of the uncoated tubing as well as on coating numbers R1, R4 and 5.

Coagulation

Blood-material contact initiates intrinsic coagulation via factors XII, XI, and further factor X which modulates prothrombin conversion. During the reaction of thrombin formation, the pro-thrombin fragment F 1+2 gets split off. The generated thrombin gets inactivated by complex-formation with antithrombin forming the so-called TAT complex. The plasma concentration of TAT is a marker for detection of coagulation activation and was measured immunochemically using a Siemens™ automatic immunoassay analyzer with ELISA.

Figure 7:
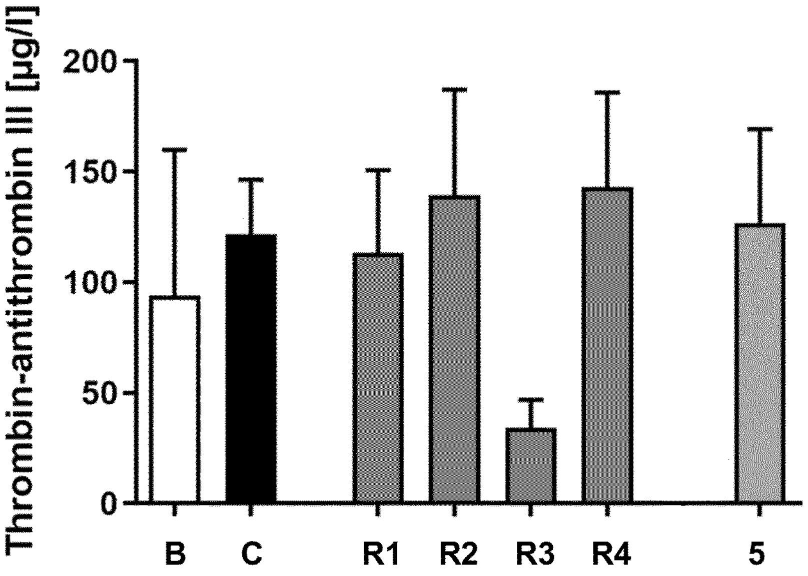
FIG. 7 is a histogram showing levels of blood concentration of coagulation factor Thrombin-Antithrombin complex (TAT) in the blood of donors at baseline and during/after a 60 min perfusion period (control tube and test item) in a Chandler-Loop model. Bars represent means and standard deviations.

The results are shown FIG. 7, where the coatings on the x-axis use the numbering set out in Table 13 above, "B" represents the Baseline and "C" represents the Control. In this investigation, we found that the coatings of the invention were comparable to the commercially available coatings numbered R1, R2 and R4. A decreased TAT concentration was only measured for coating number R3.

Platelets

Contact of blood with artificial surfaces leads to activation and alteration of platelets with consecutive loss of platelet functionality. If platelets come into contact with any artificial surface, they begin to stick to this surface. Subsequently, they start to stick together and form aggregates. The resulting drop in platelet count is a critical marker for the hemocompatibility of blood contacting devices. Platelets were counted using a cell counter (Micros 60, ABX Hematology, Montpellier, France).

Figure 8:
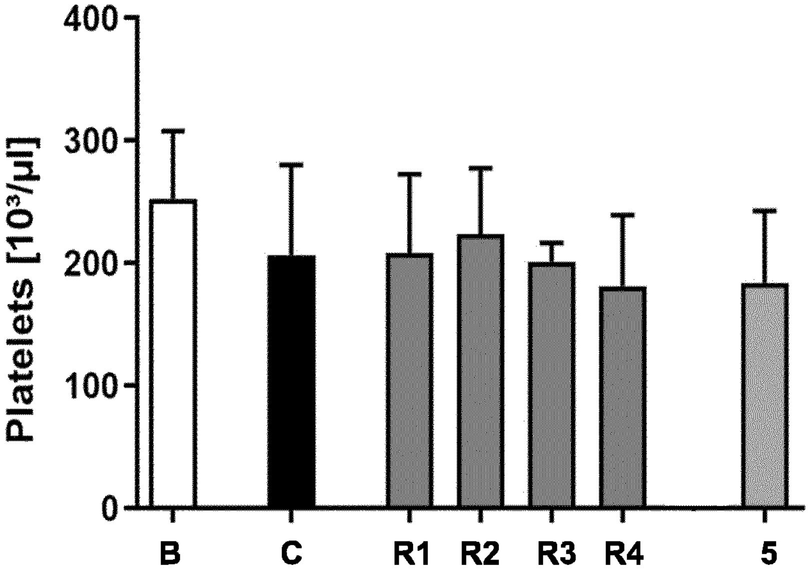
FIG. 8 is a histogram showing mean platelet counts in the blood of donors at baseline and during/after a 60 min perfusion period (control tube and test item) in a Chandler-Loop model. Bars represent means and standard deviations.

The results are shown in FIG. 8. During the 60 min test period, platelet counts mildly decreased in the control group (C). Similar values were detected in coating numbers R1 to R4 and 5.

β-Thromboglobulin (β-TG)

Activation of platelets occurs in four steps: shape change with formation of pseudopodia, adhesion, aggregation, and release of platelet factors out of the α-granules (platelet factor 4, β-TG, etc.). The concentration of β-Thromboglobulin (β-TG) in plasma corresponds with the degree of platelet activation. The concentration of β-TG was measured immunochemically (ELISA, Diagnostica Stago S.A.S, Asnières sur Seine, France).

Figure 9:
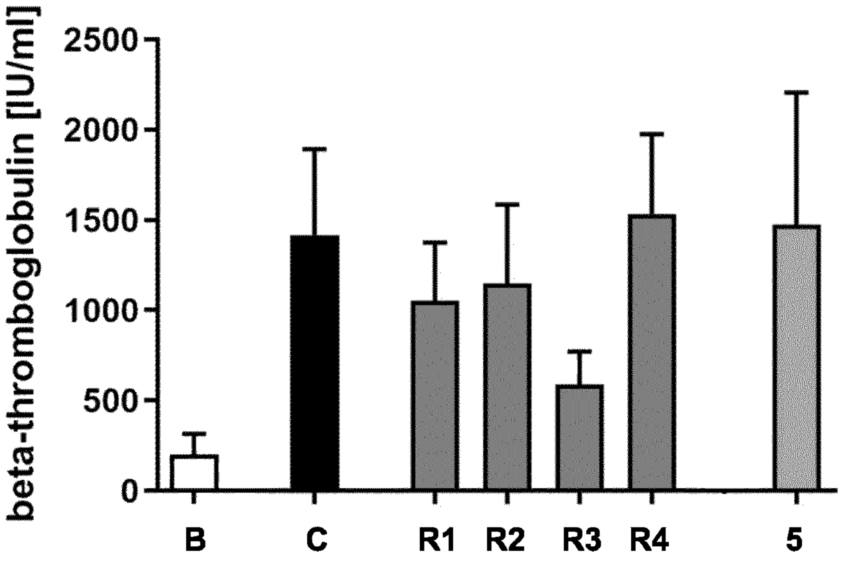
FIG. 9 is a histogram showing levels of β-Thromboglobulin (β-TG) in the blood of donors at baseline and during/after a 60 min perfusion period (control tube and test item) in a Chandler-Loop model. Bars represent means and standard deviations.

Due to circulation, the concentration of β-TG increased in the control tube indicating a mild increase in platelet activation. See the results shown in FIG. 9. Similar levels were measured in coating numbers R4 and 5. Coating numbers R1 to R3 showed a reduction in β-TG concentrations compared to these groups.

Hematological Parameters

The number of red blood cells, white blood cells, hemolysis, HGB and HCT (see below) were each measured using a cell counter (Micros 60, ABX Hematology, Montpellier, France).

Red Blood Cells (RBC) and White Blood Cells (WBC)

WBCs in contact with any artificial surface may stick to this surface and try to fight against the supposed pathologic invader. This reaction leads to a drop in WBC count and is a critical marker for the hemocompatibility of blood contacting devices. If the membranes of RBCs are destroyed by high shear forces this reaction leads to a drop in RBCs.

Figure 10:
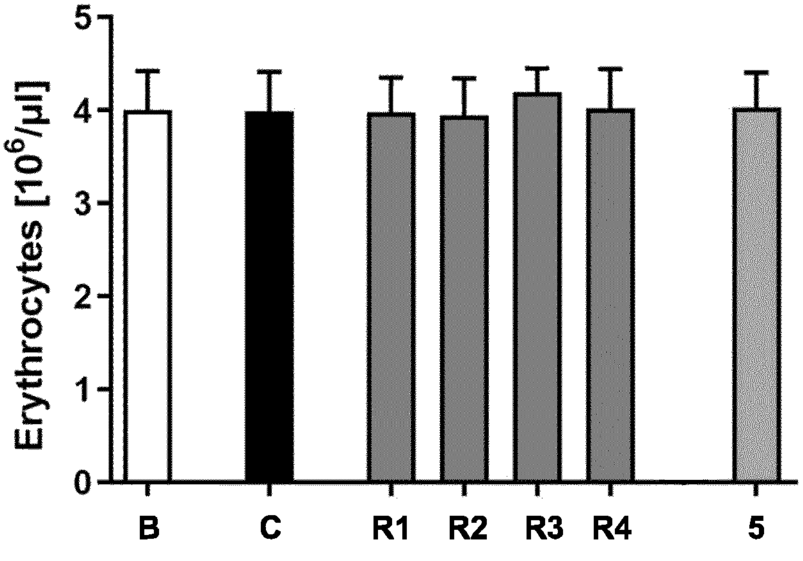
FIG. 10 is a histogram showing mean red blood cell counts in the blood of donors at baseline and during/after a 60 min perfusion period (control tube and test item) in a Chandler-Loop model. Bars represent means and standard deviations.
Figure 11:
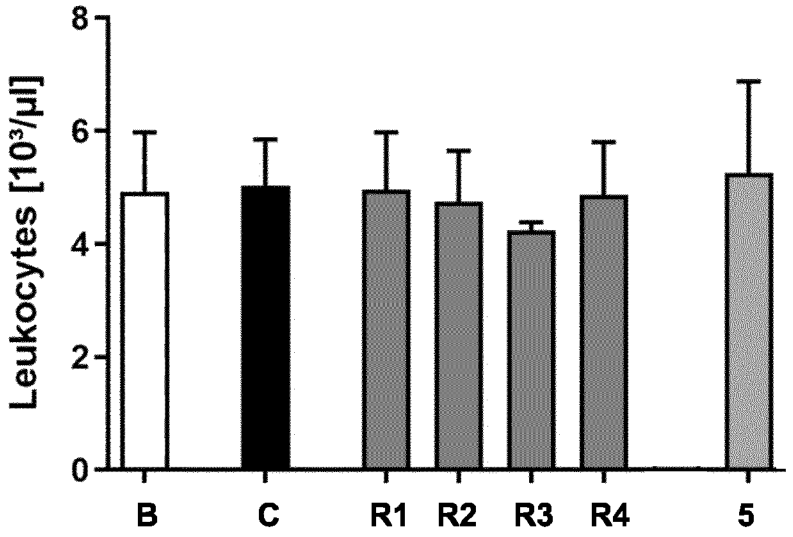
FIG. 11 is a histogram showing mean white blood cell counts in the blood of donors at baseline and during/after a 60 min perfusion period (control tube and test item) in a Chandler-Loop model. Bars represent means and standard deviations.

See the results in FIGS. 10 and 11. Erythrocyte and leukocyte counts were stable during the 60 min perfusion period.

Hemolysis

Figure 12:
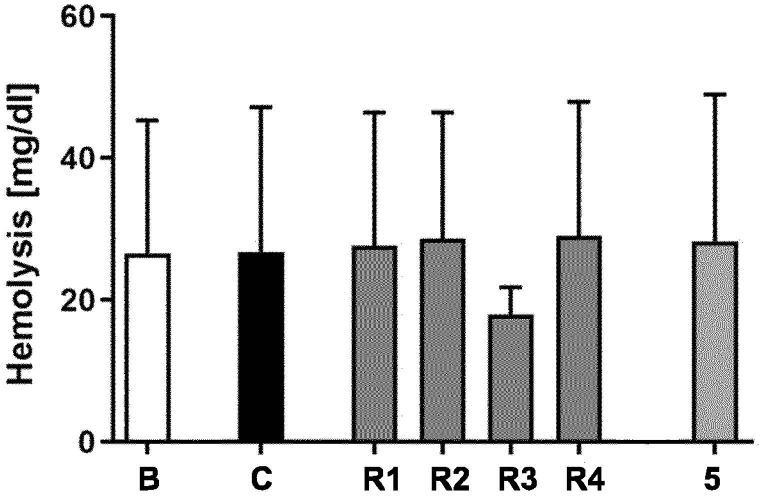
FIG. 12 is a histogram showing the mean hemolysis concentration in the blood of donors at baseline and during/after a 60 min perfusion period (control tube and test item) in a Chandler-Loop model. Bars represent means and standard deviations.

Red blood cell destruction was quantified by measuring free plasma hemoglobin. The results are shown in FIG. 12. No significant differences were detected between the test groups.

Hemoglobin (HGB) and Hematocrit (HCT)

Figure 13:
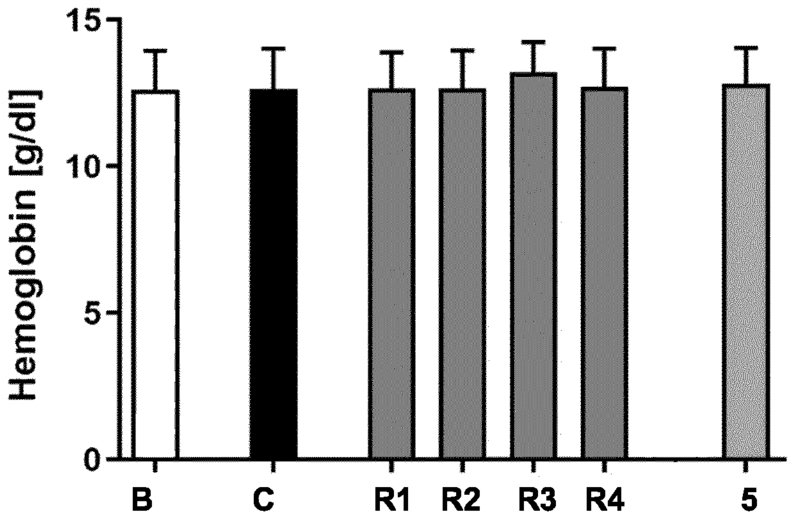
FIG. 13 is a histogram showing the mean hemoglobin concentration in the blood of donors at baseline and during/after a 60 min perfusion period (control tube and test item) in a Chandler-Loop model. Bars represent means and standard.
Figure 14:
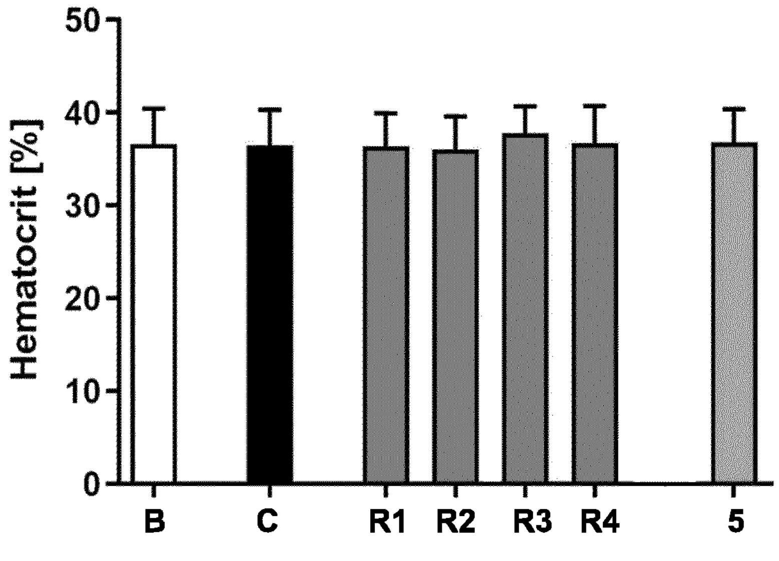
FIG. 14 is a histogram showing the mean hematocrit concentration in the blood of donors at baseline and during/after a 60 min perfusion period (control tube and test item) in a Chandler-Loop model. Bars represent means and standard deviations.

The results are shown in FIGS. 13 and 14. HGB concentration and HCT concentration were very stable during the 60 min perfusion period.

Conclusion

During the 60 min incubation period, plasma concentrations of activation markers, blood cell alterations as well as platelet adhesion demonstrated that tubes coated with the coatings of the invention (number 5) had comparable effects on several hemostatic activation cascades when compared to all of the other tubes coated with a commercially available coating. With regard to the TAT formation, which is an excellent marker for detection of coagulation activation, the measured TAT concentration induced by the coatings of the invention (number 5) was very low. Overall, the results of the hemocompatibility tests of the coatings of the invention demonstrate good hemocompatibility.

Example 3

Cytotoxicity Test Method

The method is designed to determine the biological response of mammalian cells in vitro. Murine fibroblast L929 cells were used cultured in Growth Medium: L929 cells (serum supplemented Dulbecco's MOD Medium (modified) with Earle's salts).

Samples of the coating of the invention (the sulfonic acid group modified coating) were prepared as described in Example 1. To achieve the extraction ratio required, 6 $cm^2$/ml, two samples each representing an internal surface area of 285.89 $cm^2$ were extracted separately, each with 47.7 ml of Extraction Medium: L929 cells inside of each tube, under agitation conditions. After extraction, the extractants were pooled into sterile glass bottles. The extractant was prepared from Minimum Essential Medium Eagle's (modified) with Earle's salts, supplemented with foetal calf serum (5%) and penicillin and streptomycin (50001 U). Calculations took into account the area of all major surfaces, but not the edges or any porous nature of the test article.

The interfacial area of the positive and negative control material per millilitre of final extract volume was calculated to be not less than 0.5 $cm^2$ per ml.

Positive control strips (Hatano Research Institute product code: RM-B), a polyurethane film containing 0.25% zinc dibutyldithiocarbamate (ZDBC) were used. The material was received non-sterile. The material was pre-cut to the required size (1 cm×1 cm). As each test run requires 3 pieces of material, all pieces were packaged in autoclave bags and sterilised (with 3 pieces in each bag) at 121° C. for 15 minutes. Three pieces, each measuring 1.0 cm×1.0 cm×0.05 cm, representing a total surface area of 6.6 $cm^2$, were extracted in 13.2 ml of extraction medium, under agitation condition.

For the negative control, a piece of polythene tubing (Scientific Laboratory Supplies product code: TUB3708) known not to produce a cytotoxic response in this test was used. The negative control was 2.0 cm long with an outside diameter of 0.6 cm and an inside diameter of 0.4 mm, representing a total surface area of 6.3 $cm^2$ which was extracted in 12.6 ml of extraction medium, under agitation condition.

The test procedure was performed in accordance with ISO 10993-5 and MV033. The samples and the controls were extracted at 37±1° C. for 24 hours. The following concentrations of the test article extract and positive control extract were used in the test: 100%, 50%, 25%, 13% and 6%. The cell cultures were exposed to the extracts at 37±1° C. for 24 hours. Microscopical examination of the cell cultures was made on completion of exposure to extracts without fixing and staining. The determination of cytotoxicity was performed qualitatively and observations graded numerically. The degree of cytotoxicity observed in each culture was numerically graded as follows.

TABLE 15

Qualitative morphological grading of cytotoxicity of extracts

| Grade | Reactivity | Conditions of all cultures |
|---|---|---|
| 0 | None | Discrete intracytoplasmic granules; no cell lysis, no reduction of cell growth |
| 1 | Slight | Not more than 20% of the cells are round, loosely attached, and without intracytoplasmic granules, or show changes in morphology; occasional lysed cells are present; only slight growth inhibition observable |
| 2 | Mild | Not more than 50% of the cells are round and devoid of intracytoplasmic granules: no extensive cell lysis; not more than 50% growth inhibition observable |

TABLE 15-continued

Qualitative morphological grading of cytotoxicity of extracts

| Grade | Reactivity | Conditions of all cultures |
|---|---|---|
| 3 | Moderate | Not more than 70% of the cell layers contain rounded cells or are lysed, cell layers not completely destroyed, but more than 50% growth inhibition observable |
| 4 | Severe | Nearly complete, or complete, destruction of the cell layers. |

Results

As can be seen from the results in Tables 16 and 17 for the Cell Control, Negative Control and Positive Control indicate that the test was valid. As shown in Table 18, the reactivity grading for the test sample (the invention) at a concentration of 100% was 0 under the test conditions used. The coating of the invention was non-reactive to the cell culture.

In accordance with ISO 10993-5: 2009, the achievement of a numerical grade greater than 2, based upon Table 15 is considered a cytotoxic effect.

TABLE 16

Negative control results

| Observation | Negative Control | | | Cell Control | | |
|---|---|---|---|---|---|---|
| | Rep 1 | Rep 2 | Rep 3 | Rep 1 | Rep 2 | Rep 3 |
| Extraction Reactivity (grade) | 0 | 0 | 0 | 0 | 0 | 0 |

TABLE 17

Postive control results

| Positive Control | Reactivity (grade) at Concentration % | | | | | Reactivity |
|---|---|---|---|---|---|---|
| Extraction | 100 | 50 | 25 | 13 | 6 | titre |
| Replicate 1 | 4 | 1 | 0 | 0 | 0 | 50% |
| Replicate 2 | 4 | 1 | 0 | 0 | 0 | |
| Replicate 3 | 4 | 1 | 0 | 0 | 0 | |

TABLE 18

Test extract results

| Sample | Reactivity (grade) at Concentration % | | | | | Reactivity |
|---|---|---|---|---|---|---|
| Extraction | 100 | 50 | 25 | 13 | 6 | titre |
| Replicate 1 | 0 | 0 | 0 | 0 | 0 | 50% |
| Replicate 2 | 0 | 0 | 0 | 0 | 0 | |
| Replicate 3 | 0 | 0 | 0 | 0 | 0 | |

The invention claimed is:

1. A coating for a medical device comprising:

a surface layer; and a base layer, wherein the base layer is biocompatible and comprises a protein;

wherein the surface layer comprises a copolymer consisting of a polymer chain attached to a plurality of sulfonic acid groups or sulfonate groups by a linker group, wherein the polymer chain is obtainable by polymerization of monomers selected from acrylic acid and methacrylic acid, and optionally monomers selected from maleic acid and maleimide, wherein the polymer chain includes a repeating unit represented by formula (B-1):

(B-1)

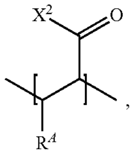

wherein:

$R^A$ is selected from H and $C_{1-6}$ alkyl;

$X^2$ is $A^2$;

$A^2$ is represented by formula (S-2):

$$—Z^2\text{-}L^2\text{-}SO_2—Y^2 \quad \text{(S-2)},$$

wherein:

$Z^2$ is selected from O, NH, and $NR^2$;

$R^2$ is selected from $C_{1-6}$ alkyl, $C_{6-10}$ aryl, and $C_{6-10}$ aryl-$C_{1-6}$ alkyl;

$Y^2$ is selected from $O^-$ and OH;

$L^2$ is represented by formula (L-2):

$$—P^2\text{-}Q^2\text{-}W^2— \quad \text{(L-2)},$$

wherein:

$P^2$ is selected from a single bond, $C_{1-10}$ alkylene, $C_{2-10}$ alkenylene, $C_{2-10}$ alkynylene, and phenylene;

$Q^2$ is selected from a single bond, O, NH, $NR^{2C}$, and phenylene;

$W^2$ is selected from a single bond, $C_{1-10}$ alkylene, $C_{2-10}$ alkenylene, $C_{2-10}$ alkynylene, and phenylene; and $R^{2C}$ is selected from $C_{1-6}$ alkyl, $C_{6-10}$ aryl, and $C_{6-10}$ aryl-$C_{1-6}$ alkyl.

2. The coating according to claim 1, wherein $Z^2$ is selected from O and NH.

3. The coating according to claim 1, wherein $P^2$ is selected from $C_{1-10}$ alkylene, $C_{2-10}$ alkenylene, and $C_{2-10}$ alkynylene; $Q^2$ is a single bond; and $W^2$ is a single bond.

4. The coating according to claim 1, wherein $P^2$ is selected from $C_{1-10}$ alkylene, $C_{2-10}$ alkenylene, and $C_{2-10}$ alkynylene; $Q^2$ is selected from O, NH, and $NR^{2C}$; and $W^2$ is a single bond.

5. The coating according to claim 1, wherein $R^A$ is selected from H and methyl.

6. A medical device having a surface coated with the coating according to claim 1.

7. The coating according to claim 1, wherein the protein is human albumin.

8. The coating according to claim 7, wherein the human albumin is recombinant human albumin.

9. The coating according to claim 7, wherein the human albumin is covalently bonded to the polymer chain.

10. The coating according to claim 1, wherein the surface layer is in the form of a hydrogel.

11. The coating according to claim 1, wherein the polymer chain has a number average molecular weight of 1,000 g/mol to 10,000 g/mol.

12. The coating according to claim 1, wherein the polymer chain includes a repeating unit represented by formula (A-1):

(A-1)

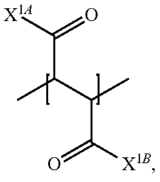

wherein:

$X^{1A}$ is selected from $O^-$, OH, $OR^{1A}$, $NH_2$, $NHR^{1A}$, and $A^{1A}$;

$X^{1B}$ is selected from $O^-$, OH, $OR^{1B}$, $NH_2$, $NHR^{1B}$, and $A^{1B}$;

each of $R^{1A}$ and $R^{1B}$ is independently selected from $C_{1-6}$ alkyl, $C_{6-10}$ aryl, and $C_{6-10}$ aryl-$C_{1-6}$ alkyl;

each of $A^{1A}$ and $A^{1B}$ is independently represented by formula (S-1):

$$—Z^1\text{-}L^1\text{-}SO_2—Y^1 \quad \text{(S-1)},$$

wherein:

$Z^1$ is selected from O, NH, and $NR^1$;

$R^1$ is selected from $C_{1-6}$ alkyl, $C_{6-10}$ aryl, and $C_{6-10}$ aryl-$C_{1-6}$ alkyl;

$Y^1$ is selected from $O^-$ and OH;

$L^1$ is represented by formula (L-1):

$$—P^1\text{-}Q^1\text{-}W^1— \quad \text{(L-1)},$$

wherein:

$P^1$ is selected from a single bond, $C_{1-10}$ alkylene, $C_{2-10}$ alkenylene, $C_{2-10}$ alkynylene, and phenylene;

$Q^1$ is selected from a single bond, O, NH, $NR^{1C}$, and phenylene;

$W^1$ is selected from a single bond, $C_{1-10}$ alkylene, $C_{2-10}$ alkenylene, $C_{2-10}$ alkynylene, and phenylene; and $R^{1C}$ is selected from $C_{1-6}$ alkyl, $C_{6-10}$ aryl, and $C_{6-10}$ aryl-$C_{1-6}$ alkyl.

13. The coating according to claim 12, wherein each $Z^1$ is selected from O and NH.

14. The coating according to claim 12, wherein each $P^1$ is selected from $C_{1-10}$ alkylene, $C_{2-10}$ alkenylene and $C_{2-10}$ alkynylene; each $Q^1$ is a single bond; and each $W^1$ is a single bond.

15. The coating according to claim 12, wherein each $P^1$ is selected from $C_{1-10}$ alkylene, $C_{2-10}$ alkenylene, and $C_{2-10}$ alkynylene; each $Q^1$ is selected from O, NH, and $NR^{1C}$; and each $W^1$ is a single bond.

* * * * *